(12) United States Patent
Hwu et al.

(10) Patent No.: US 7,723,111 B2
(45) Date of Patent: May 25, 2010

(54) ACTIVATED DUAL SPECIFICITY LYMPHOCYTES AND THEIR METHODS OF USE

(75) Inventors: Patrick Hwu, Potomac, MD (US); Michael H. Kershaw, Rockville, MD (US); Steven A. Rosenberg, Potomac, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/803,578

(22) Filed: Mar. 9, 2001

(65) Prior Publication Data

US 2003/0026790 A1 Feb. 6, 2003

(51) Int. Cl.
*C12N 15/00* (2006.01)
*C12N 5/08* (2006.01)
*A61K 48/00* (2006.01)

(52) U.S. Cl. .................. 435/455; 424/93.1; 424/93.2; 424/93.21; 435/372; 435/372.3; 435/375

(58) Field of Classification Search ................ 435/325; 424/93.1, 93.2, 93.21
See application file for complete search history.

(56) References Cited

U.S. PATENT DOCUMENTS

| 5,061,620 | A |  | 10/1991 | Tsukamoto et al. |  |
| 5,359,046 | A |  | 10/1994 | Capon et al. |  |
| 5,399,346 | A |  | 3/1995 | Anderson et al. |  |
| 5,830,755 | A | * | 11/1998 | Nishimura et al. | .......... 435/335 |
| 5,844,075 | A | * | 12/1998 | Kawakami et al. | .......... 530/326 |
| 6,407,221 | B1 | * | 6/2002 | Capon et al. | ............... 536/23.4 |
| 6,410,319 | B1 | * | 6/2002 | Raubitschek et al. | ..... 435/343.1 |

FOREIGN PATENT DOCUMENTS

| EP |  | 0203403 | 4/1986 |
| EP |  | 0340793 | 5/1989 |
| WO | WO | 92/10591 | 6/1992 |
| WO | WO | 92/15322 | 9/1992 |
| WO | WO | 93/19163 | 9/1993 |
| WO | WO | 95/06409 | 3/1995 |
| WO | WO | 00/23573 | 4/2000 |

OTHER PUBLICATIONS

Dorland's Medical Dictionary definition of "allogeneic."*
Stedman's Medical Dictionary definition of "endogenous."*
The abstract from Shiloni et al. (Oct. 1993, Cancer immunology, immunotherapy, vol. 37, p. 286-292).*
Cole Cancer Research, 1997, vol. 57, 5320-5327.*
Darcey (J. Immunol., 2000, vol. 164, p. 3705-3712).*
Haynes (J. Immunol., 2001, vol. 166, p. 182-187).*
Dakappagari (Cancer Res. 2000, vol. 60, p. 3782-3789).*
Weijtens, (J. Immunol., 1996, vol. 157, p. 836-843).*
Robbins (Cancer Res. 1991, vol. 51, No. 14, p. 3657-62) abstract only.*
Beecham et al, J Immunother 2000; 23:332-43.*
Terheyden et al, J Immunol 2000;164:6633-9.*
Munz et al, J Immunol 1999;162:25-34.*
Altenschmidt et al, J Immunol 1997;159:5509-15.*
T helper & T cytotoxic cell. Wikipedia, 2006.*
Clay et al, J Immunol 1999;163:507-13.*
Janeway et al., Antigen Presentation to T lymphocytes. Immunobiology v2001, Total 3 pages.*
DJ Cole et al. "T-cell Receptor Usage and Epitope Mapping of HLA-A2 Restricted, Melanoma Reactive CTL Clones and Oligoclonal Lines", *The Faseb Journal*, Abstracts, Apr. 9-13, 1995.
Hwu, et al. (1994) "The Use of Gene-modified Tumor-Infiltrating Lymphocytes for Cancer Therapy", vol. 716, *Annals of the New York Academy of Sciences*, pp. 188-199, May 31, 1994.
Hwu, et al. (1993) "Lysis of Ovarian Cancer Cells by Human Lymphocytes Redirected with a Chimeric Gene Composed of an Antibody Variable Region and the Fc Receptor γ Chain", *The Journal of Experimental Medicine*, vol. 178, pp. 361-366, Jul. 1993.
Hwu, et al. (1993) "Functional and Molecular Characterization of Tumor-Infiltrating Lymphocytes Transduced with Tumor Necrosis Factor α cDNA for the Gene Therapy of Cancer in Humans", *The Journal of Immunology*, Vo. 150, pp. 4104-4115, No. 9, May 1993.
Nishimura et al. (1994) "T-Cell Receptor Repertoire in Tumor-infiltrating Lymphocytes, Analysis of Melanoma-Specific Long-Term Lines", *Journal of Immunotherapy*, vol. 16, pp. 85-94, (1994).
Cole et al. (1994) "Identification of MART-1-specific T-Cell Receptors: T Cells Utilizing Distinct T-Cell Receptor Variable and Joint Regions Recognize the Same Tumor Epitope", *Cancer Research*, vol. 54, pp. 5265-5268, Oct. 15, 1994.
Cole et al. (1995) "Characterization of the Functional Specificity of a Cloned T-Cell Receptor Heterodimer Recognizing the MART-1 Melanoma Antigen", *Cancer Research*, vol. 55, pp. 748-752, Feb. 15, 1995.
Shilyansky et al. (1994) "T-cell Receptor Usage by Melanoma-specific Clonal and Highly Oligoclonal Tumor-infiltrating Lymphocyte Lines", *Proc. Natl. Acad Sci USA*, vol. 91, pp. 2829-2833, Mar. 1994.
Treisman, et al. (1995) "Interleukin-2-transduced Lymphocytes Grow in an Autocrine Fashion and Remain Responsive to Antigen", *Blood*, vol. 35, No. 1, pp. 138-145, Jan. 1, 1995.
Herlyn, et al. (1984) "Efficient Selection of Human Tumor Growth-Inhibiting Monoclonal Antibodies", *Journal of Immunological Methods*, vol. 73, pp. 157-167, 1984.
Hwu, et al. (1995) "In vivo Antitumor Activity of T Cells Redirected with Chimeric Antibody/T-Cell Receptor Genes", *Cancer Research*, vol. 55, Aug. 1, 1995.

(Continued)

*Primary Examiner*—Q. Janice Li
(74) *Attorney, Agent, or Firm*—Leydig, Voit & Mayer

(57) ABSTRACT

The present invention relates to preventive, therapeutic, and diagnostic compositions and methods employing lymphocytes having T-cell receptors and chimeric receptors. In particular, the invention relates to pre-selected dual-specificity lymphocytes having endogenous T-cell receptors and chimeric T-cell receptors that recognize a strong antigen and tumor associated antigens where the pre-selected population of adoptively transferred lymphocytes is activated by in vivo immunization, thereby increasing the effectiveness of adoptive immunotherapy.

15 Claims, 17 Drawing Sheets

OTHER PUBLICATIONS

Lanier, et al. (1989) "Co-association of CD3ζ with a Receptor (CD16) for IgG Fc on Human Natural Killer Cells", *Nature*, vol. 342, pp. 803-804, Dec. 14, 1989.

Eshhar, et al. (1993) "Specific Activation and Targeting of Cytotoxic Lymphocytes Through Chimeric Single Chains Consisting of Antibody-Binding Domains and the γ or ζ Subunits of the Immunoglobulin and T-cell Receptors", *Proc. Natl Acad. Sci*, USA, vol. 90, pp. 720-724, Jan. 1993.

Kuwana, et al., (1987) "Expression of Chimeric Receptor Composed of Immunoglobulin-Derived V Regions and T-Cell Receptor Derived C Regions", *Biochemical and Biophysical Research Communications*, pp. 960-968, vol. 149, No. 3 Dec. 1987.

Huston, et al. (1988) "Protein Engineering of Antibody Binding Sites: Recovery of Specific Activity in an Anti-Digoxin Single Chain Fv Analogue Produced in *Escherichia coli*", *Proc Natl. Acad Sci*, USA, pp. 5879-5883, Aug. 1988.

Romeo, et al. (1991) "Cellular Immunity to HIV Activated by CD 4 Fused to T-Cell or Fc Receptor Polypeptides", *Cell*, vol. 64, pp. 1037-1046, Mar. 8, 1991.

Gross, et al. (1989) "Generation of Effector T-Cells Expressing Chimeric T-Cell Receptor with Antibody Type-Specificity", *Transplantation Proceedings*, vol. 21, No. 1 Feb. 1989, pp. 127-130.

Becker, et al. "Expression of a Hybrid Immunoglobulin—T Cell Receptor Protein in Transgenic Mice", *Cell*, vol. 58, pp. 911-921, Sep. 8, 1989.

Goverman et al., "Chimeric Immunoglobulin T Cell Receptor Proteins Form Functional Receptors: Implications for T Cell Receptor Complex Formation and Activation", *Cell*, vol. 60, pp. 929-939, Mar. 23, 1990.

Gross et al. "Expression of Immunoglobulin T-Cell Receptor Chimeric Molecules as Functional Receptors with Antibody Type Specificity", *Proc. Natl. Acad Sci*, USA, vol. 86, pp. 10024-10028, Dec. 1989.

Wang, et al. "Limited T-Cell Antigen Receptor Repertoire in Tumor-Infiltrating Lymphocyte and Inhibition of Experimental Lung Metastasis of Murine Melanoma by Anti-TcR Antibody", *The Journal of Immunology*, vol. 154, pp. 1797-1803, 1995.

Rosenberg, S., "The Gene Therapy of Cancer", *Aids Research and Human Retroviruses*, vol. 10, No. Suppl. 3, 1994. Abstract.

Hwu et al. (1994) "The Genetic Modification of T-Cells for Cancer Therapy: An Overview of Laboratory and Clinical Trials", *Cancer Detection and Prevention*, vol. 18(1), pp. 43-50.

Dakappagari et al., *Cancer Res.*, 60(14), 3782-3789 (2000).

Darcy et al., *J. Immunol.*, 164(7), 3705-3712 (2000).

Haynes et al., *J. Immunol.*, 166(1), 182-187 (2001).

Roberts et al., *Blood*, 84(9), 2878-2889 (1994).

Weijtens et al., *J Immunol.*, 157(2), 836-843 (1996).

Weijtens et al., *Int. J. Cancer*, 77(2), 181-187 (1998), abstract.

Weijtens et al., *Gene Ther.*, 5(9), 1195-1203 (1998), abstract.

GenBank Accession No. D13555 (Dec. 28, 1993).

GenBank Accession No. S52322 (May 8, 1993).

GenBank Accession No. U88067 (Feb. 26, 1997).

Abken et al., *Cancer Treat Rev.*, 23, 97-112 (1997).

Calogero et al., *J Immunother.*, 23, 393-400 (2000).

Geiger et al., *42nd Annual Meeting of the American Society of Hematology, Session: 894-II*, 429a (2000).

Hombach et al., *J. Lab. Med.*, 24(3), 126-134 (2000).

Maher et al., *42nd Annual Meeting of the American Society of Hematology, Session 315-II*, 294a (2000).

Parker et al., *Hum. Gene Ther.*, 11, 2377-2387 (2000).

Quinn et al., *Hum. Gene Ther.*, 9, 1457-1467 (1998).

\* cited by examiner

ACTIVATED DUAL SPECIFICITY LYMPHOCYTES AND THEIR METHODS OF USE

FIELD OF THE INVENTION

The field of the present invention relates generally to compositions and methods for the treatment or prevention of diseases in mammals. More specifically, this invention relates to pre-selected dual-specificity lymphocytes having endogenous T-cell receptors and/or chimeric T-cell receptors that recognize a strong antigen and tumor associated antigens and to preventative, diagnostic and therapeutic applications which employ these lymphocytes.

BACKGROUND OF THE INVENTION

Classic modalities for the treatment of diseases such as human cancers, autoimmune diseases, viral, bacterial, parasitic and fungal diseases include surgery, radiation chemotherapy, antibiotics or combination therapies. However, these therapies are not effective against a majority of these diseases. Alternate therapies for preventing or treating human diseases are greatly needed. In the past decade immunotherapy and gene therapy utilizing T-lymphocytes have emerged as new and promising methods for treating human disease, in particular human cancers.

The T cell receptor for antigen (TCR) is responsible for the recognition of antigen associated with the major histocompatibility complex (MHC). The TCR expressed on the surface of T cells is associated with an invariant structure, CD3. CD3 is assumed to be responsible for intracellular signaling following occupancy of the TCR by ligand.

The T cell receptor for antigen-CD3 complex (TCR/CD3) recognizes antigenic peptides that are presented to it by the proteins of the major histocompatibility complex (MHC). Complexes of MHC and peptide are expressed on the surface of antigen presenting cells and other T cell targets. Stimulation of the TCR/CD3 complex results in activation of the T cell and a consequent antigen-specific immune response. The TCR/CD3 complex plays a central role in the effector function and regulation of the immune system.

Two forms of T cell receptor for antigen are expressed on the surface of T cells. These contain either $\alpha/\beta$ heterodimers or $\gamma/\delta$ heterodimers. T cells are capable of rearranging the genes that encode the $\alpha$, $\beta$, $\gamma$ and $\delta$ chains of the T cell receptor. T cell receptor gene rearrangements are analogous to those that produce functional immunoglobulins in B cells and the presence of multiple variable and joining regions in the genome allows the generation of T cell receptors with a diverse range of binding specificities. Each $\alpha/\beta$ or $\gamma/\delta$ heterodimer is expressed on the surface of the T cell in association with four invariant peptides. These are the $\gamma$, $\delta$ and $\epsilon$ subunits of the CD3 complex and the zeta chain. The CD3 $\gamma$, $\delta$ and $\epsilon$ polypeptides are encoded by three members of the immunoglobulin supergene family and are found in a cluster on human chromosome 11 or murine chromosome 9. The zeta chain gene is found separately from other TCR and CD3 genes on chromosome 1 in both the mouse and human. Murine T cells are able to generate a receptor-associated $\eta$ chain through alternative splicing of the zeta mRNA transcript. The CD3 chains and the zeta subunit do not show variability, and are not involved directly in antigen recognition.

All the components of the T cell receptor are membrane proteins and consist of a leader sequence, externally-disposed N-terminal extracellular domains, a single membrane-spanning domain, and cytoplasmic tails. The $\alpha$, $\beta$, $\gamma$ and $\delta$ antigen-binding polypeptides are glycoproteins. The zeta chain has a relatively short ectodomain of only nine amino acids and a long cytoplasmic tail of approximately 110 amino acids. Most T cell receptor $\alpha/\beta$ heterodimers are covalently linked through disulphide bonds, but many $\gamma$ $\delta$ receptors associate with one another non-covalently. The zeta chain quantitatively forms either disulphide-linked $\zeta$-$\eta$ heterodimers or zeta-zeta homodimers.

Another example of a type of receptor on cells of the immune system is the Fc receptor. The interaction of antibody—antigen complexes with cells of the immune system results in a wide array of responses, ranging from effector functions such as antibody-dependent cytotoxicity, mast cell degranulation, and phagocytosis to immunomodulatory signals such as regulating lymphocyte proliferation, phagocytosis and target cell lysis. All these interactions are initiated through the binding of the Fc domain of antibodies or immune complexes to specialized cell surface receptors on hematopoietic cells. It is now well established that the diversity of cellular responses triggered by antibodies and immune complexes results from the structural heterogeneity of Fc receptors (FcRs).

FcRs are defined by their specificity for immunoglobulin isotypes. Fc receptors for IgG are referred to as Fc$\gamma$R, for IgE as Fc$\epsilon$R, for IgA as Fc$\alpha$R, etc. Structurally distinct receptors are distinguished by a Roman numeral, based on historical precedent. Three groups of Fc$\gamma$Rs, designated Fc$\gamma$RI, Fc$\gamma$RII, and Fc$\gamma$RIII are now recognized. Two groups of Fc$\epsilon$R have been defined; these are referred to as Fc$\epsilon$RI and Fc$\epsilon$RII. Structurally related although distinct genes within a group are denoted by A, B, C. Finally, the protein subunit is given a Greek letter, such as Fc$\gamma$RIIIA$\alpha$, Fc$\gamma$RIIIA$\gamma$.

Considerable progress has recently been made in defining the heterogeneity for IgG and IgE Fc receptors (Fc$\gamma$R, Fc$\epsilon$R) through their molecular cloning. These studies make it apparent that Fc receptors share structurally related ligand binding domains, but differ in their transmembrane and intracellular domains which presumably mediate intracellular signaling. Thus, specific Fc$\gamma$Rs on different cells mediate different cellular responses upon interaction with an immune complex. The structural analysis of the Fc$\gamma$Rs and Fc$\epsilon$RI has also revealed at least one common subunit among some of these receptors. This common subunit is the $\gamma$ subunit, which is similar to the $\zeta$ or $\eta$ chain of the TCR/CD3, and is involved in the signal transduction of the Fc$\gamma$RIII and Fc$\epsilon$RI.

The low affinity receptor for IgG (Fc$\gamma$RIIIA), is composed of the ligand binding CD16$\alpha$ (Fc$\gamma$RIIIA$\alpha$) polypeptide associated with the $\gamma$ chain (Fc$\gamma$RIIIA$\gamma$). The CD16 polypeptide appears as membrane anchored form in polymorphonuclear cells and as transmembrane form (CD16TM) in NK. The Fc$\gamma$RIIIA serves as a triggering molecule for NK cells.

Another type of immune cell receptor is the IL-2 receptor. This receptor is composed of three chains, the $\alpha$ chain (p55), the $\beta$ chain (p75) and the $\gamma$ chain. When stimulated by IL-2, lymphocytes undergo proliferation and activation.

Antigen-specific effector lymphocytes, such as tumor specific T cells (Tc), are very rare, individual-specific, limited in their recognition spectrum and difficult to obtain against most malignancies. Antibodies, on the other hand, are readily obtainable, more easily derived, have wider spectrum and are not individual-specific. The major problem of applying specific antibodies for cancer immunotherapy lies in the inability of sufficient amounts of monoclonal antibodies (mAb) to reach large areas within solid tumors. In practice, many clinical attempts to recruit the humoral or cellular arms of the immune system for passive anti-tumor immunotherapy have not fulfilled expectations. While it has been possible to obtain anti-tumor antibodies, their therapeutic use has been limited so far to blood-borne tumors [Lowder, J. N. et al. *Cancer Surv.* 4:359-375 (1985); Waldmann, T. A. *Science* 252:1657-1662 (1991)] primarily because solid tumors are inaccessible to sufficient amounts of antibodies [Jain, R. K. *J. Natl. Cancer Inst.* 81:64-66 (1989)]. The use of effector lymphocytes in adoptive immunotherapy, although effective in selected solid tumors, suffers on the other hand, from a lack of specificity (such as in the case of lymphokine-activated killer cells (LAK cells) [Mule, J. J. et al. *Science* 225:1487-1489 (1984)] which are mainly NK cells) or from the difficulty in recruiting tumor-infiltrating lymphocytes (TILs) and expanding such specific T cells for most malignancies [Rosenberg, S. A. et al. *Science* 233:1318-1321 (1986)]. Yet, the observations that TILs can be obtained in melanoma and renal cell carcinoma tumors, that they can be effective in selected patients and that foreign genes can function in these cells [Rosenberg, S. A. *J. Clin. Oncol.* 10:180-199 (1992)] demonstrate the therapeutic potential embodied in these cells.

A strategy which has been developed (European Published Patent Application No. 0340793) allows one to combine the advantage of the antibody's specificity with the homing, tissue penetration, cytokine production and target-cell destruction of T lymphocytes and to extend, by ex vivo genetic manipulations, the spectrum of anti-tumor specificity of T cells. Chimeric T cell receptor (cTCR) genes composed of the variable region domain (Fv) of an antibody molecule and the constant region domain of the antigen-binding TCR chains, i.e., the α/β or γ/δ chains have been expressed in T cells and found to be functionally active. Adoptive immunotherapies using tumor infiltrating lymphocytes and IL-2 have been developed for some cancers. These therapies have resulted in significant long-term responses in some patients with melanoma.

In an effort to broaden the applicability of adoptive immunotherapy to common cancers, such as, for example, ovarian, breast and colon cancer treatments that redirect the immune reactivity of lymphocytes to antigens recognized by monoclonal antibodies have been developed. To do this, retroviral vectors that encode chimeric receptor genes consisting of the variable regions of a monoclonal antibody joined to the transmembraneous and cytoplasmic domains of a T-cell receptor (TCR) signaling chain have been utilized. Using this approach, the safety of the administration of these chimeric receptor-transduced lymphocytes has been demonstrated. However, a need for improving the effectiveness of the chimeric receptor-transduced lymphocytes exists.

Thus, one object of the present invention is to produce an activated chimeric receptor-transduced lymphocyte capable of binding to and obliterating cancer cells.

SUMMARY OF THE INVENTION

One particular object of the present invention is to increase the effectiveness of adoptive immunotherapy by increasing the persistence and/or activity of adoptively transferred T cells by activating a pre-selected population of adoptively transferred lymphocytes with in vivo immunization.

Another objective of the invention is to create dual specific T cells by genetic modification so that each individual T cell is reactive with both a strong antigen, such as, for example an alloantigen or other foreign agent, and the tumor. The strong antigen is used both to expand and activate the cells in vitro and in vivo.

The present invention relates to a composition comprising a population of T cells transduced with a chimeric receptor gene and pre-selected for reactivity with a strong antigen.

Another embodiment of the present invention comprises a lymphocyte having a TCR directed to a specific strong antigen and a chimeric T-cell receptor directed to a tumor antigen, wherein the lymphocyte has been activated in vivo by the strong antigen. Such cells exhibit strong anti-tumor response and provide a recipient of such cells with a protection from tumor challenge, i.e. prophylactic response, and an anti-tumor treatment.

The method of treating a patient with therapeutically-activated dual-specificity lymphocytes comprises the steps of expanding a patient's lymphocytes with one or more specific strong antigens ex vivo, transducing the lymphocytes with a chimeric receptor gene, introducing the transduced lymphocytes into the patient and immunizing the patient with the strong antigen(s) in vivo. A preferred embodiment of the present method utilizes an alloantigen as the strong antigen. Another preferred embodiment utilizes a virus or other foreign antigen as the strong antigen.

The present invention also relates to a method of treating a patient with dual specificity lymphocytes having reactivity to one or more pre-selected strong antigens comprising the steps of administering an effective amount of such lymphocytes to a patient and immunizing the patient with the strong antigen.

The present invention relates to activated dual specific lymphocytes containing chimeric genes suitable to endow lymphocyte cells with antibody-type specificity and T-cell receptors specific for one or more pre-selected strong antigens. Various types of lymphocytes are suitable, for example, natural killer cells, helper T cells, suppressor T cells, cytotoxic T cells, lymphokine activated cells, subtypes thereof and any other cell type which can express chimeric receptor chain.

The present invention further relates to pharmaceutical, prophylactic and curative compositions containing an effective quantity of such cells.

DESCRIPTION OF THE DRAWINGS

FIGS. 11A-11E show that the T cells express the chimeric MOv-γ receptor, as demonstrated by the shift in peak on the X-axis. FIGS. 11F-11J demonstrate by FACS whether the clone is CD4 or CD8.

DETAILED DESCRIPTION OF THE INVENTION

Figure 1:
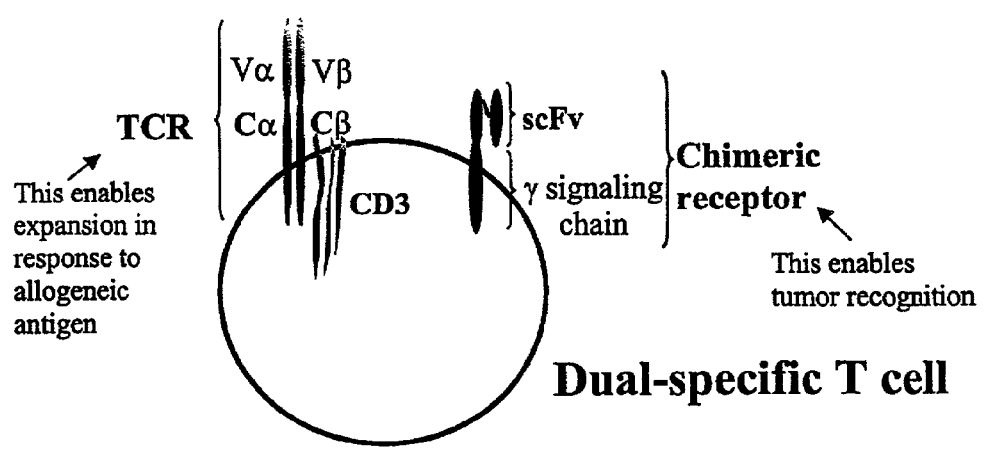
FIG. 1 shows a model of the dual-specific T cell created by genetic modification such that each individual T cell has specificity for both the strong antigen/immunogen and tumor. The chimeric receptor enables tumor recognition and comprises single-chain antibody variable regions (scFv) connected to TCR signaling chains, such as the γ chain of the Fc receptor.

For the purpose of a more complete understanding of the invention, the following definitions are described herein. Nucleic acid sequences include, but are not limited to, DNA, RNA or cDNA. Substantially homologous as used herein refers to substantial correspondence between the nucleic acid sequence for the V-J or V-D-J junctional sequences for the α and β chains of the tumor antigen specific T-cell receptors provided herein and that of any other nucleic acid sequence. By way of example, substantially homologous means about 50-100% homology, preferably by about 70-100% homology, and most preferably about 90-100% homology between the nucleic acid sequences and that of any other nucleic acid sequence. In addition, substantially homologous as used herein also refers to substantial correspondence between the amino acid sequence of the V-J or V-D-J junctional sequences of the antigen specific T-cell receptors provided herein and that of any other amino acid sequence.

Major Histocompatibility Complex (MHC) is a generic designation meant to encompass the histo-compatibility antigen systems described in different species including the human leukocyte antigens (HLA). The term cancer includes but is not limited to, melanoma, epithelial cell derived cancers, lung cancer, colon cancer, ovarian cancer, breast cancer, kidney cancer, prostate cancer, brain cancer, or sarcomas.

The term melanoma includes, but is not limited to, melanomas, metastatic melanomas, melanomas derived from either melanocytes or melanocyte related nevus cells, melanocarcinomas, melanoepitheliomas, melanosarcomas, melanoma in situ, superficial spreading melanoma, nodular melanoma, lentigo maligna melanoma, acral lentiginous melanoma, invasive melanoma or familial atypical mole and melanoma (FAM-M) syndrome. The aforementioned cancers can be treated, assessed or diagnosed by methods described in the present application.

The lymphocytes of the present invention are pre-selected for TCRs having reactivity with specific antigens. These antigens are preferably strong antigens. The term "strong antigen" as it is referred to herein relates to an antigen capable of inducing proliferation of pre-selected adoptively transferred T cells. Examples of such antigens include but are not limited to alloantigens, viral agents and other foreign agents. Allogeneic agents or "alloantigens" are antigens derived from genetically non-identical members of the same species. Allogeneic tissues, cells, proteins, peptides, nucleic acids and/or other cellular components may be used to select an individual or subpopulation of lymphocytes. Examples of viral agents are well-known in the art, and include, but are not limited to, Epstein Barr virus and the Flu-virus and proteins, peptides, nucleic acids and other cellular components derived therefrom. Examples of other strong antigens include foreign proteins such as serum proteins from other species including bovine.

"Dual specificity lymphocytes" as that phrase is used herein refers to lymphocytes capable of reacting with both a tumor antigen and a pre-selected strong antigen. The tumor antigen reactivity may be conferred by genetically modifying lymphocytes with a chimeric T cell receptor gene encoding a binding site for the tumor antigen. Tumor antigen reactivity may also be conferred by native TCR itself. Reactivity with the pre-selected strong antigen(s) is preferably conferred by in vitro expansion of the isolated population of lymphocytes by specific T cell activation using one or more pre-selected strong antigens.

"Chimeric receptor gene" refers to any receptor gene encoding a protein containing an extracellular recognition/binding site and transmembrane and intracellular portions capable of translating the binding of a ligand to the recognition site to specific intracellular activities. Preferably, the chimeric receptor gene encodes sequences for T-cell receptors or parts thereof which recognize tumor associated antigens and/or function to translate extracellular/cytoplasmic signal to intracellular activities in T-cells. One example of such a chimeric receptor gene encodes a single chain variable region from a monoclonal antibody joined to the Fc receptor chain capable of mediating T-cell receptor signal transduction. Another preferred chimeric receptor comprises an antibody variable region joined to the cytoplasmic region of CD28 from a T cell or a similar region which can provide a T cell with co-stimulation signals.

Additional examples of immune cell trigger molecules are any one of the IL-2 receptor (IL-2R) p55 (α) or p75 (β) or γ chains, especially the p75 and γ subunits which are responsible for signaling T cell and NK proliferation.

Further candidate receptor molecules for creation of scFv chimeras in accordance with the present invention include the subunit chains of Fc receptors. In the group of NK-stimulatory receptors, the most attractive candidates are the γ- and CD16α-subunits of the low affinity receptor for IgG, FcγRIII. Occupancy or cross-linking of FcγRIII (either by anti-CD16 or through immune complexes) activates NK cells for cytokine production, expression of surface molecules and cytolytic activity [Unkeless, J. C. et al., *Annu. Rev. Immunol.* 6:251-281 (1988); Ravetch, J. V. and Kinet, J. P. *Annu. Rev. Immunol.* 9:457-492 (1991)]. In NK cells, macrophages, and B and T cells, the FcγRIII appears as a heterooligomeric complex consisting of a ligand-binding α chain associated with a disulfide-linked γ or zeta chain. The FcγRIIIA signalling gamma chain [Wirthmuller, V. et al., *J. Exp. Med.* 175:1381-1390 (1992)] serves also as part of the FcεRI complex, where it appears as a homodimer, is very similar to the CD3 zeta chain, and in fact can form heterodimers with it in some cytolytic T lymphocytes (CTL) and NK cells [Orloff, D. G., et al. *Nature* (London) 347:189-191 (1990); Lanier, L. G., et al. *J. Immunol.* 146:1571-1576 (1991); Vivier, E., et al. *J. Immunol.* 147:4263-4270 (1991)]. Most recently prepared chimeras between these polypeptides and the CD4 [Romeo, C. and Seed, B. *Cell* 64:1037-1046 (1991)], the CD8 [Irving, B. A. and Weiss, A. *Cell* 64:891-901 (1991)], IL-2 receptor chain [Letourneur, F. and Klausner, R. D. *Proc. Natl. Acad. Sci. USA* 88:8905-8909 (1991)] or CD16 extracellular domains, proved to be active in signaling T cell stimulation even in the absence of other TCR/CD3 components.

In one embodiment, the chimeric receptor genes encode amino acid sequences which provide for the V-J or V-D-J junctional regions or parts thereof for the alpha and beta chains of the T-cell receptor which recognize tumor associated antigens. In general, the chimeric T-cell receptors recognize or bind tumor associated antigens presented in the context of MHC Class I. Many different tumor associated antigens are known to the skilled artisan. A tumor antigen can be defined as a molecule that can be used to target therapy against a tumor and includes those antigens only found on tumor cells (i.e. tumor specific), those which are expressed on tumor cells and on limited normal tissues, i.e. differentiation antigens (including cancer-testis antigens) and those which are over-expressed on tumor cells compared to the expression on a wide variety of normal tissues (i.e. over-expressed antigens). Examples of over-expressed antigens include, but are not limited to, Folate binding protein (FBP), Erb-B2, GD-2, HMW-MAA, G250, TAG-72, NY-ESO-1, carcino-embryonic antigen and alpha-fetoprotein. Differentiation antigens include, for example, Tyrosinase, MART-1, MAGE and gp100 of melanoma. Tumor-specific antigens include, for example, mutant Ras, mutant p53, mutant Erb-B2 of a wide variety of tumors including breast and colon. Any of these tumor antigens can serve as the binding agent for the TCR or chimeric receptor. The choice of which antigen to target is within the skill of the ordinary artisan, and is based upon the specific tumor being targeted.

In one preferred embodiment, the tumor associated antigens recognized by the receptors of this invention are melanoma antigens. By way of example, melanoma specific T-cell receptors may recognize melanoma antigens in the context of HLA-A2.1 or HLA-A 1. Examples of melanoma antigens which are recognized by the chimeric receptors include, but are not limited to, MART-1, or peptides thereof or gp-100 or peptides thereof. In a preferred embodiment the chimeric receptor regonizes or binds to the MART-1 peptide, in particular epitopes M9-1 (TTAEEAAGI) (SEQ ID NO: 1), M9-2 (AAGIGILTV) (SEQ ID NO:2), M10-3 (EAAGIGILTV) (SEQ ID NO 3), and M10-4 (AAGIGILTVI) (SEQ ID NO: 4) (shown in single letter amino acid code) or gp-100 peptide epitopes.

The chimeric receptor is provided as a recombinant DNA molecule comprising all or part of the T-cell receptor nucleic acid sequence and a vector. The nucleic acid sequences encoding the α and β chains of a T-cell receptor of the present invention may be placed in a single expression vector. Alternatively the α chain and the β chain may each be placed in a separate expression vector. Expression vectors suitable for use in the present invention may comprise at least one expression control element operationally linked to the nucleic acid sequence. The expression control elements are inserted in the vector to control and regulate the expression of the nucleic acid sequence. Examples of expression control elements include, but are not limited to, lac system, operator and promoter regions of phage lambda, yeast promoters and promoters derived from polyoma, adenovirus, retrovirus, cytomegalovirus (CMV), SRα, MMLV, SV40 or housekeeping promoters such as phosphoglycerol kinase (PGK) and β actin. Additional preferred or required operational elements include, but are not limited to, leader sequences, termination codons, polyadenylation signals and any other sequences necessary or preferred for the appropriate transcription and subsequent translation of the nucleic acid sequence in the host system. It will be understood by one skilled in the art that the correct combination of required or preferred expression control elements will depend on the host system chosen. It will further be understood that the expression vector may contain additional elements necessary for the transfer and subsequent replication of the expression vector containing the nucleic acid sequence in the host system. Examples of such elements include, but are not limited to, origins of replication and selectable markers and long terminal repeats (LTR) and internal ribosomal entry site (IRES). The expression vector may also include a leader peptide sequence. It will further be understood by one skilled in the art that such vectors are easily constructed using conventional methods [Ausubel et al., (1987) in "Current Protocols in Molecular Biology", John Wiley and Sons, New York, New York] or commercially available.

Alternatively, the chimeric receptor gene may comprise a first gene segment encoding the single chain Fv receptor (scFv) of a specific antibody, i.e., DNA sequences encoding the variable regions of the heavy and light chains ($V_H$ and $V_L$, respectively) of the specific antibody, linked by a flexible linker, and a second gene segment which comprises a DNA sequence encoding partially or entirely the transmembrane and cytoplasmic, and optionally the extracellular, domains of a lymphocyte-triggering molecule corresponding to a lymphocyte receptor or part thereof. Thus, the scFvR design may be advantageous over the two-chain version of the receptor. It requires the expression of only one gene instead of the gene pair required for the cTCR, thereby providing simpler construction and transfection.

The scFv domain may preferably be joined to the immune cell triggering molecule such that the scFv portion will be extracellular when the chimera is expressed. This is accomplished by joining the scFv either to the very end of the transmembrane portion opposite the cytoplasmic domain of the trigger molecule or by using a spacer which is either part of the endogenous extracellular portion of the triggering molecule or from other sources. The chimeric molecules of the present invention have the ability to confer on the immune cells on which they are expressed MHC nonrestricted antibody-type specificity. Thus, a continuous polypeptide of antigen binding and signal transducing properties can be produced and utilized as a targeting receptor on immune cells. In vivo, cells expressing these genetically engineered chimeric receptors will home to their target, will be stimulated by it to attract other effector cells, or, by itself, will mediate specific destruction of the target cells. In a preferred embodiment, the target cells are tumor cells and the scFv domain is derived from an antibody specific to an epitope expressed on the tumor cells. It is expected that such anti-tumor cytolysis can also be independent of exogenous supply of IL-2, thus providing a specific and safer means for adoptive immunotherapy.

Besides the specific receptor chains specifically mentioned herein, the single chain Fv chimeras can be made by joining the scFv domain with any receptor or co-receptor chain having a similar function to the disclosed molecules, e.g., derived from granulocytes, B lymphocytes, mast cells, macrophages, etc. The distinguishing features of desirable immune cell trigger molecules comprise the ability to be expressed autonomously (i.e., as a single chain), the ability to be fused to an extracellular domain such that the resultant chimera is expressed on the surface of an immune cell into which the corresponding gene was genetically introduced, and the ability to take part in signal transduction programs secondary to encounter with a target ligand.

The construction options for the production of chimeric T-cell receptor genes and their corresponding proteins can be found in U.S. Pat. No. 5,830,755 and U.S. Application Publication No. 2002/0137697 A1, both of which are incorporated herein by reference in toto. In addition, Hwu et al. (Can. Res. (1995) 55:3369-3373) and Wang et al. (Nat. Med. (1998) 492:168) describe details of introducing a chimeric receptor gene into cells and treating tumors therewith. These references are incorporated herein by reference.

Specific expansion and specific activation of the T cells containing the chimeric T-cell receptor gene are important parts of the present invention. In one embodiment, the specific expansion step amplifies an individual or a subpopulation of T cells whose endogenous TCR is directed to the strong antigen(s) used to expand the T cells. In this way, T cells which react with the antigen(s) are selected out and amplified from a mixed population of T cells originally obtained from the patient. The expanded lymphocytes are transduced with a chimeric receptor gene. These pre-selected, transduced T cells are introduced into a patient, and the patient is immunized with the strong antigen(s). This in vivo immunization step serves to activate the pre-selected adoptively transferred T cells and to target the lymphocytes to the cancer antigen through the chimeric receptor.

In a preferred embodiment of the invention, patients undergo leukapheresis to obtain peripheral blood lymphocytes (PBL). The lymphocytes are separated from other cells. Various methods of separation are known to the artisan and can be utilized. One preferred separation technique employs centrifugation on a Ficoll cushion. The preferred host cells transformed with all or part of the chimeric receptor nucleic acid sequences may include JURKAT-cells, T-lymphocytes, peripheral blood cells such as peripheral blood lymphocytes (PBL) and peripheral blood mononuclear cells (PBMC), dendritic cells, monocytes, stem cells, natural killer (NK) cells or macrophages.

Candidate immune cells to be endowed with antibody specificity using this approach are: NK cells, lymphokine-activated killer cells (LAK), cytotoxic T cells, helper T cells, and the various subtypes of the above. These cells can execute their authentic natural function and can serve, in addition, as carriers of foreign genes designated for gene therapy, and the chimeric receptor shall serve in this case to direct the cells to their target. This approach can be applied also to anti-idiotypic vaccination by using helper T cells expressing chimeric receptors made of Fv of antiidiotypic antibodies.

The cells are activated with one or more preselected antigens. Any strong antigen, i.e. one that is capable of inducing proliferation of the adoptively transferred lymphocytes, may be utilized for the activation/selection step. The lymphocytes are preferably exposed to the strong antigen for greater than one hour in the case of proteins and virus or for at least 24 hours, preferably, continuously, for allogeneic cells as strong antigens. The strong antigen is provided up to a concentration of 1 millimolar when proteins, peptides or cellular components are used or at a ratio of one dual specific T-cell to 1-1000 infectious viral particles or between 1 and 100 allogeneic cells per each dual-specific T-cell. A combination of several stimuli may optionally be included in the activation/selection mixture. One preferred embodiment utilizes a donor's PBLs as an allogeneic agent. When donor PBLs are used, selection is carried out by co-culture of irradiated donor PBMC with patient PBMC at a ratio preferably with the range of 2:1 to 5:1.

These cells are transduced with a chimeric receptor gene. "Transduction" or introduction of foreign DNA into the immune cells may be carried out by any manner known in the art, such as, for example, microinjection, electroporation, transduction, retroviral transduction or transfection using DEAE-dextran, lipofection, calcium phosphate, particle bombardment mediated gene transfer or direct injection of nucleic acid sequences encoding the chimeric receptors or other procedures known to one skilled in the art [Sambrook et al. (1989) in "Molecular Cloning. A Laboratory Manual", Cold Spring Harbor Press, Plainview, N.Y.]. One preferred method of transduction follows the method described in Hwu, et al., (1993) *J. Immunol.* 150:4104-4115. One preferred method of transduction resuspends the lymphocyte preparation in a retroviral supernatant at a concentration range of $1\times10^2$ to $1\times10^{10}$ per ml, more preferably at a range of $1\times10^4$ to $1\times10^8$, most preferably at a concentration of $1\times10^6$. Transduction may preferably be followed by a selection step, such as for example using an antibiotic selection marker on the chimeric receptor gene construct, such as the neomycin resistance gene.

The preselected transduced lymphocytes may be cultured for several days. Between days 14-21, it may be desirable to screen the cells for specific cytokine release against ovarian tumor antigens and/or assay for phenotype integrity. At this time, it may also be desirable to restimulate the lymphocyte population with the strong antigen. Restimulation using a strong antigen is preferably carried out at a similar concentration as used for the initial stimulation for a similar time period. If donor cells are used as the allogeneic agent, restimulation is preferably carried out at a ratio of 0.5:1 to 4:1, more preferably at a ratio of 1:1 to 2:1 (donor:patient). These cells can be directly reintroduced into the patient or can be frozen for future use, i.e. for subsequent administrations to this patient.

Upon expansion of lymphocytes in IL-2 containing media, patients receive preselected transduced lymphocytes intravenously. Optionally, the patient may also receive IL-2, preferably after the lymphocyte infusion. It is preferable that the IL-2 be provided at a dosage range of 1200 IU/kg to 1,200,000 IU/kg, more preferably at 120,000 IU/kg every 12 hours. After the first administration, patients may again receive preselected, transduced lymphocytes intravenously with or without similar doses of IL-2. Dual specificity lymphocytes are administered at a dosage range of $1\times10^6$ to $1\times10^{15}$, more preferably $1\times10^8$ to $1\times10^{11}$, most preferably $3\times10^9$ to $5\times10^{10}$ cells. Further details on dosage and frequency of cells are provided in U.S. Pat. No. 5,399,346, which is incorporated herein by reference, in toto.

The present invention provides a method of inhibiting or preventing the growth of tumor cells by exposing tumor cells to the dual specificity lymphocytes provided herein. The dual specificity lymphocytes may be used for either prophylactic or therapeutic purposes. When provided prophylactically, the dual specificity lymphocytes is provided in advance of any evidence or symptom in the mammal due to cancer, in particular, melanoma. The prophylactic use of the dual specificity lymphocytes serves to prevent or attenuate cancer, in particular melanoma, in a mammal. When provided therapeutically, dual specificity lymphocytes are provided after the onset of the disease in the mammal. The therapeutic administration of the dual specificity lymphocytes serves to attenuate the disease.

Cell-based immunotherapy currently utilizes the adoptive transfer to patients of tumor specific TIL which are generically expanded ex vivo [Rosenberg S. A. 1992. *J. Clin. Oncol.*, 10:80; Rosenberg S. A., et al. *N. Engl. J. Med.*, 319: 1676; Hwu P., et al. 1993. *J. Exp. Med.*, 178:361]. T-cell specificity may be redirected by combination of the in vitro transfer of the nucleic acid sequences encoding the tumor associated antigen specific T-cell receptors and selective expansion of the lymphocytes with one or more strong antigens. By way of example, a heterogenous population of T-cells, such as TIL, may be made more effective by conferring anti-tumor reactivity to non-specific T-cell populations within the TIL, and selective expansion of T lymphocytes to amplify T lymphocytes reactive with one or more pre-selected strong antigens.

Cells that can be modified to produce dual specificity lymphocytes include, but is not limited to, lymphocytes, cytotoxic T-lymphocytes, hematopoietic stem cells, monocytes, stem cells, peripheral blood and natural killer cells. In a preferred embodiment, T-cells can be genetically modified to express the tumor antigen specific T-cell receptors. Constructs containing all or parts of the nucleic acid sequences encoding the chimeric T-cell receptors may be introduced in T-lymphocytes by conventional methodology. By way of example such methods include, but are not limited to, calcium phosphate transfection, electroporations, lipofections, transduction by retroviruses, injection of DNA, particle bombardment and mediated gene transfer use of a retroviral vector, viral vectors, transduction by viral co-culturing with a producer cell line. Preferably, the construct or constructs carrying the nucleic acid sequences encoding the chimeric T-cell receptors are introduced into the T-cells by transduction with viral supernatant or co-cultivation with a retroviral producer cell line. Examples of vectors that may be used include, but are not limited to, defective retroviral vectors, adenoviral vectors, vaccinia viral vectors, fowl pox viral vectors, or other viral vectors [Mulligan, R. C., (1993) *Science* 260:926-932]. Eukaryotic expression vectors GLEN [Treisman, J., et al., *Blood*, 85:139; Morgan et al. (1992) *Nucleic Acids Res.* 20:1293-1299], LXSN [Miller, A. D., et al. *Methods Enzymol.*, 217:581-599 (1993); Miller, A. D., et al. *BioTechniques*, 7:980-988 (1989); Miller, A.D., et al., Mol. Cell Biol., 6:2895-2902 (1986); Miller, A. D. *Curr. Top. Microbiol. Immunol.*, 158:1-24 (1992)], and SAM-EN [Treisman, J., et al., *Blood*, 85:139] may also be used. Individual constructs carrying the genes coding for the alpha and beta chains that comprise the receptor may be introduced into the T-lymphocytes or alternatively, an individual construct carrying the nucleic acid sequences encoding for both the α and β chains of the T-cell receptor may be in a single construct. Preferably, a retroviral vector, for example a vector with the murine moloney leukemia viral LTR promoting transcription of the T-cells receptor genes is used. In a preferred embodiment non-replicating retroviral vectors are used. Alternatively, the genes can be expressed using an internal housekeeping promoter, such as that from the phosphoglycerol kinase (PGK) gene.

The α and β chains of the T-cell receptor may either be expressed on separate retroviral vectors, or on the same retroviral vector, separated by an internal ribosomal entry site (IRES) [Treisman, J., et al., *Blood*, 85:139; Morgan, R. A., et al., *Nucleic Acids. Res.*, 20:1293-1299 (1992)]. Using an IRES-containing vector, allows both T-cell receptor genes to be translated from a single RNA message. Examples of where T-lymphocytes can be isolated, include but are not limited to, peripheral blood cell lymphocytes (PBL), lymph nodes, or tumor infiltrating lymphocytes (TIL), or blood. Such lymphocytes can be isolated from the individual to be treated or from a donor by methods known in the art and cultured in vitro [Kawakami, Y. et al. (1989) *J. Immunol.* 142: 2453-3461]. Alternatively, a single chain Fv receptor gene may be constructed and used as the chimeric receptor gene.

The T-cells may be incubated with a retroviral producer cell line carrying retroviral expression vectors or with viral supernatant. Viability of the lymphocytes may be assessed by conventional methods, such as trypan blue dye exclusion assay. The genetically modified lymphocytes expressing the desired melanoma specific T-cell receptor may then be administered to a mammal, preferably a human, in need of such treatment in a therapeutically effective amount. The dosing regimes or ranges of lymphocytes used in the conventional tumor infiltrating lymphocyte (TIL) therapy [Rosenberg, et al. (1994) *J. Natl. Canc. Inst.*, Vol. 86:1159] may be used as general guidelines for the doses or number of T-lymphocytes to be administered to mammal in need of such treatment. By way of example, a range of about $1\times10^{10}$ to about $1\times10^{11}$ T-cells for each cycle of therapy may be administered in the methods provided herein. Examples of how these antigen specific T-cells can be administered to the mammal include but are not limited to, intravenously, intraperitoneally or intralesionally. Parameters that may be assessed to determine the efficacy of these transduced T-lymphocytes include, but are not limited to, production of immune cells in the mammal being treated or tumor regression. Conventional methods are used to assess these parameters. Such treatment can be given in conjunction with cytokines or gene modified cells [Rosenberg, S. A. et al. (1992) *Human Gene Therapy*, 3: 75-90; Rosenberg, S. A. et al. (1992) *Human Gene Therapy*, 3: 57-73] chemotherapy or active immunization therapies. One of skill in the art will appreciate that the exact treatment schedule and dosages, or amount of T-lymphocytes to be administered may need to be optimized for a given individual.

This invention also relates to pharmacological compositions comprising the dual specificity lymphocytes. The formulations of the present invention, both for veterinary and for human use, comprise each component individually or as a composition as described above, together with one or more pharmaceutically acceptable carriers and, optionally, other therapeutic ingredients. The carrier(s) must be "acceptable" in the sense of being compatible with the other ingredients of the formulation and not deleterious to the recipient thereof. The formulations may conveniently be presented in unit dosage form and may be prepared by any method known in the pharmaceutical art.

Preparation of the pharmaceutical compositions include the step of bringing into association the active ingredient with the carrier which constitutes one or more accessory ingredients. In general, the formulations are prepared by uniformly and intimately bringing into association the active ingredient with liquid carriers or finely divided solid carriers or both, and then, if necessary, shaping the product into the desired formulation.

Formulations suitable for intravenous intramuscular, subcutaneous, or intraperitoneal administration conveniently comprise sterile aqueous solutions of the active ingredient with solutions which are preferably isotonic with the blood of the recipient. Such formulations may be conveniently prepared by dissolving solid active ingredient in water containing physiologically compatible substances such as sodium chloride (e.g. 0.1-2.0M), glycine, and the like, and having a buffered pH compatible with physiological conditions to produce an aqueous solution, and rendering said solution sterile. These may be present in unit or multi-dose containers, for example, sealed ampoules or vials.

The formulations of the present invention may incorporate a stabilizer. Illustrative stabilizers are polyethylene glycol, proteins, saccharide, amino acids, inorganic acids, and organic acids which may be used either on their own or as admixtures. These stabilizers are preferably incorporated in an amount of 0.11-10,000 parts by weight per part by weight of each component or the composition. If two or more stabilizers are to be used, their total amount is preferably within the range specified above. These stabilizers are used in aqueous solutions at the appropriate concentration and pH. The specific osmotic pressure of such aqueous solutions is generally in the range of 0.1-3.0 osmoles, preferably in the range of 0.8-1.2. The pH of the aqueous solution is adjusted to be within the range of 5.0-9.0, preferably within the range of 6-8. In formulating each component separately or as a composition of the present invention, anti-adsorption agent may be used.

Additional pharmaceutical methods may be employed to control the duration of action. Controlled release preparations may be achieved through the use of polymer to complex or absorb the cells or their derivatives. The controlled delivery may be exercised by selecting appropriate macromolecules (for example polyester, polyamino acids, polyvinyl, pyrrolidone, ethylenevinylacetate, methylcellulose, carboxymethylcellulose, or protamine sulfate) and the concentration of macromolecules as well as the methods of incorporation in order to control release. Another possible method to control the duration of action by controlled-release preparations is to incorporate the 9-cis-retinoic acid or derivatives thereof alone or in combination with antineoplastic agents thereof into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxymethylcellulose or gelatin-microcapsules and poly(methylmethacylate) microcapsules, respectively, or in colloidal drug delivery systems, for example, liposomes, albumin microspheres, microemulsions, nanoparticles, and nanocapsules or in macroemulsions.

When oral preparations are desired, the component may be combined with typical carriers, such as lactose, sucrose, starch, talc magnesium stearate, crystalline cellulose, methyl cellulose, carboxymethyl cellulose, glycerin, sodium alginate or gum arabic among others.

The administration of the compositions or of each individual component of the present invention may be for either a prophylactic or therapeutic purpose. The methods and compositions used herein may be used alone in prophylactic or therapeutic uses or in conjunction with additional therapies known to those skilled in the art in the prevention or treatment of cancer. Alternatively the methods and compositions described herein may be used as adjunct therapy. Veterinary uses are also intended to be encompassed by this invention.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The invention will now be illustrated by the following non-limiting examples.

EXAMPLES

Example 1

Ineffective Treatment of Cancer Patients

Figure 2:
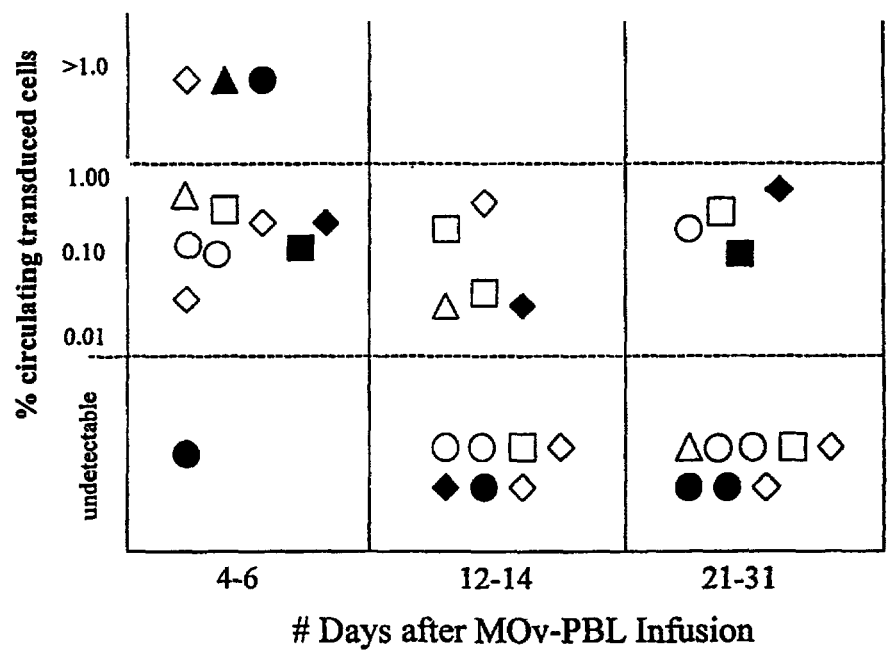
FIG. 2 shows the results of treating 8 advanced ovarian cancer patients with MOv-PBL infusion. Specifically, treatment was measured by the percentage of circulating MOv-γ transduced lymphocyte cells following MOv-PBL infusion.

Previously, chimeric receptors against ovarian cancer (MOv-γ) were found to be functional in primary T cells in vitro and in vivo [Hwu, P., et al. *J. Exp. Med.,* 178:361-366, 1993; Hwu, P., et al., *Cancer Res.,* 55:3369-3373, 1995]. The effects of treating eight patients with advanced ovarian cancer with T cells transduced with chimeric receptor genes derived from a monoclonal antibody against ovarian cancer, MOv-18 alone, and without any specificity were observed. Tumor-infiltrating lymphocytes (TIL) or anti-CD3 stimulated peripheral blood lymphocytes (PBL) retrovirally transduced with the MOv18 chimeric receptor gene (MOv-γ) were generated in large numbers of MOv-PBL which remained highly reactive against ovarian cancer cells in vitro prior to infusion. Patients were treated with up to $5 \times 10^{10}$ transduced PBL for CD3 in combination with systemic IL-2 (120,000 CU/kg). The results of this clinical trial demonstrated that cells were directed to lung, liver, and spleen, but did not specifically localize at tumor sites. Despite specific in vitro reactivity of MOv-PBL against ovarian cancer cells, none of the patients responded to the lymphocyte infusion. The number of circulating transduced cells following MOv-PBL infusion was determined. Between 4-6 days following MOv-PBL infusion, between 0.01 and 1% circulating transduced cells were detected; however, between 12-31 days, the majority of transduced cells were undetectable. FIG. 2 shows the percentage of circulating transduced cells during the course of the treatment after MOv-PBL infusion.

Example 2

Functionality of MOv-PBL After Ineffective Treatment of Cancer Patients

In order to address the question as to why patients transduced with chimeric receptor genes did not respond to treatment although 10% of transduced cells were found circulating in one patient's PBMC analyzed after 5 days post MOv-PBL infusion, the functionality of MOv-PBL after cell transfer was determined. Fresh uncultured PBMC from the day 5 post MOv-PBL infusion time point were co-cultured with ovarian cancer cells or melanoma cells (888 mel or 1300 mel). Supernatants were assayed for IFN-γ by enzyme-linked immunosorbent assay (ELISA) and lysates were analyzed for IFN-γ mRNA using Taqman. No significant IFN-γ release was seen using the fresh day 5 PBMC. To reisolate the adoptively transferred MOv-PBL, the PBMC from day 5 were cultured in G418 (for neomycin resistant selection), anti-CD3, and IL-2. After 17 days, the culture was highly enriched for reisolated MOv-PBL (69% positive for gene) that were capable of specifically producing large amounts of cytokine in response to ovarian tumor cells. As measured by IFN-γ release (pg/ml), Table 1 shows that MOv-PBL retained their ability to recognize tumor after adoptive transfer. The NV PBL group did not result in IGROV or melanoma reactivity. The NV PBL and G418 group also did not result in significant IGROV, 888 mel, or 1300 mel reactivity. Both cultured MOv-PBL and the reisolated PBL were significantly IGROV-reactive. These results indicate that MOv-PBL retained their ability to recognize tumor after adoptive transfer, although culturing was necessary to observe anti-tumor reactivity.

TABLE 1

| GROUP | IFN-γ Release (pg/ml) | | |
|---|---|---|---|
| | IGROV | 888 mel | 1300 mel |
| NV PBL | 0 | 0 | 0 |
| NV PBL + G418 | 0 | 49 | 0 |
| MOv-γ transduced PBL | 3582 | 3 | 14 |
| Reisolated PBL | 2912 | 0 | 192 |

Example 3

In vivo Expansion of Alloreactive Cultured T Cells in Murine Models

Figure 3A:
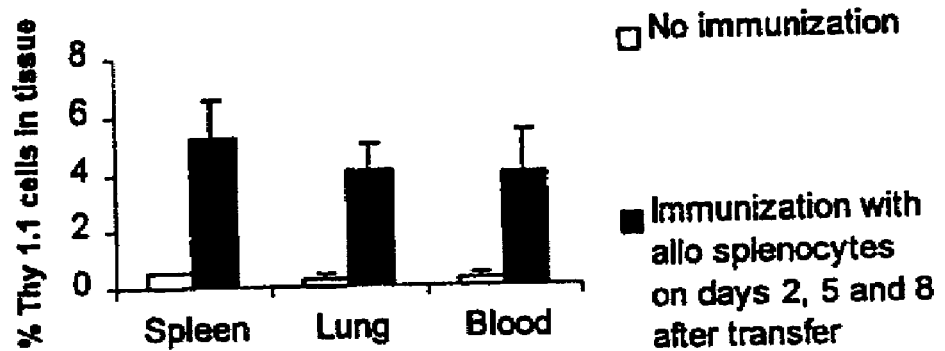
FIGS. 3A and 3B show the in vivo effects of allogeneic immunization of adoptively transferred T cells in mice spleen, lung, and blood upon immunization with allo-splenocytes (A) and allo-DC (dendritic cells; B) as a measure of Thy 1.1 cells in tissue.
Figure 3B:
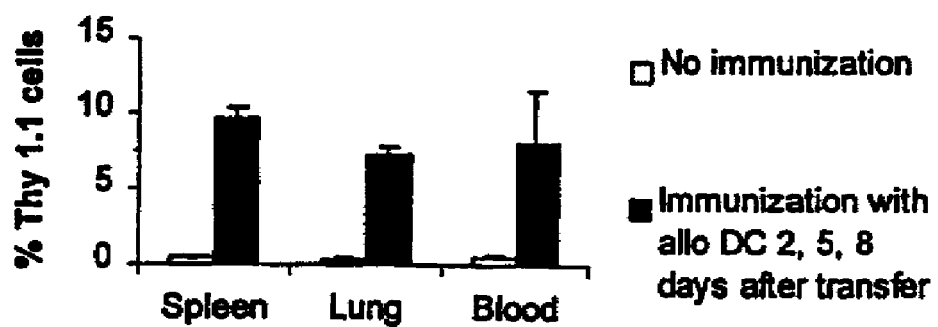

In order to determine the effects of allogeneic immunization of adoptively transferred T cells, anti-allogeneic mouse (C57BL/6) T cells were raised in a mixed lymphocyte reaction (MLR) for 7 days and restimulated for 6 additional days. Thy 1.1+ alloreactive (H2-b anti-H2-d) T cells were generated and expanded and $1 \times 10^7$ cells were adoptively transferred into congenic C57BL/6 mice (Thy 1.2) by intravenous injection. The C57BL/6 mice were immunized with allogeneic antigen presenting cells from BALB/c mice on days 2, 5, and 8 after transfer. Where stimulators, for example, either allogeneic splenocytes or allogeneic dendritic cells (DC), were used to immunize the mice. Stimulators are strong antigenic agents which activate responder cells, for example lymphocytes. There were 3 mice per condition group. Tissues (spleen, lung, and blood) were harvested on day 11 and Thy 1.1 cells were quantified following staining and fluorescence-activated cell sorter (FACS) analysis. The percent of Thy 1.1 cells in tissue was measured by comparing those immunized with allogeneic splenocytes and allogeneic DC. Adoptively transferred, cultured alloreactive T cells were found to expand in vivo following immunization with allogeneic antigen presenting cells and increased the survival of in vitro-cultured, adoptively transferred allo-reactive T cells upon immunization with allogeneic cells (FIGS. 3A and 3B).

Example 4

Generation of Dual Specificity Mouse T Cells

Figure 4:
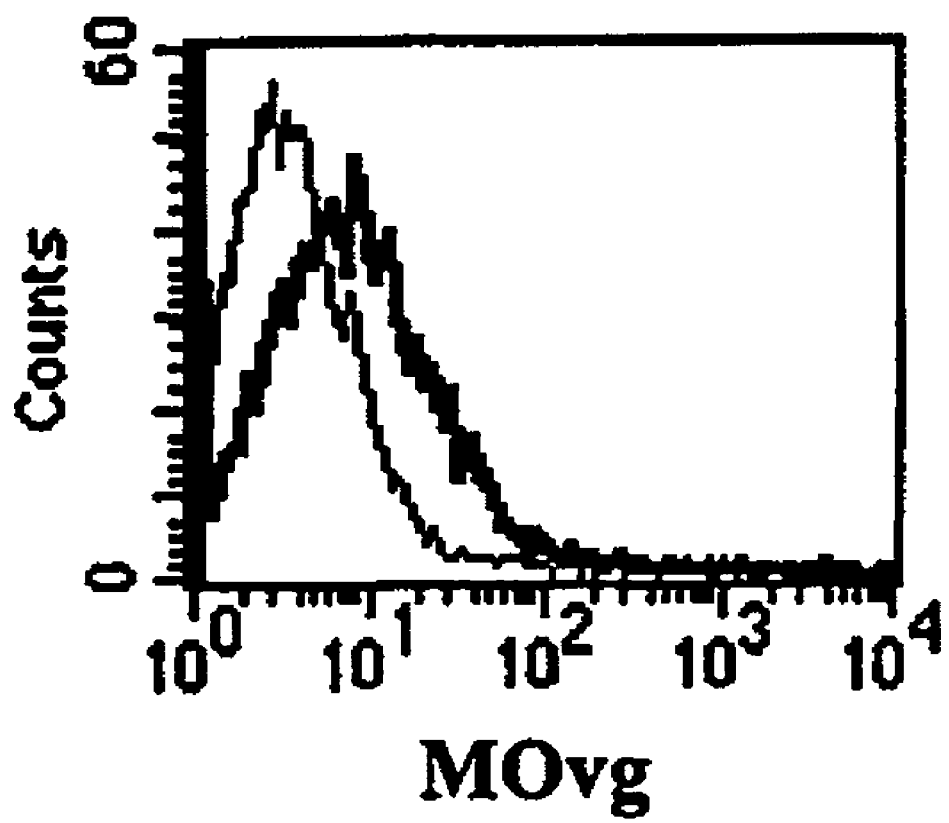
FIG. 4 shows the phenotypic results of dual specific mouse T cells, where these T cells express the chimeric MOv-γ.

C57BL/6 mice T cells ($2 \times 10^7$) were raised in a mixed leukocyte reaction (MLR) in 24 well plates and 10 CU/ml IL-2 with restimulation on day 7. G418 (0.5 mg/ml) was added for 6 days until day 13 and assayed for MOv-γ expression and IFN-γ secretion in response to various target cells. The results of Table 2 and FIG. 4 show that dual specificity T cells expressing chimeric MOv-γ with significant anti-allogeneic and anti-FBP activity as measured by IFN-γ (pg/ml) was generated.

TABLE 2

| | Non-transduced T | | |
|---|---|---|---|
| | Media | cells | MOv-γ T cells |
| Media | 0 | 0 | 0 |
| CT26 (allogeneic H-2d) | 0 | 65,200 | 138,700 |
| 24JK (H-2b) | 0 | 0 | 0 |
| 24JK-FBP | 0 | 0 | 5200 |
| 888 mel | 0 | 0 | 0 |
| IGROV (ovarian FBP +) | 0 | 0 | 37,500 |

Example 5

Figure 5:
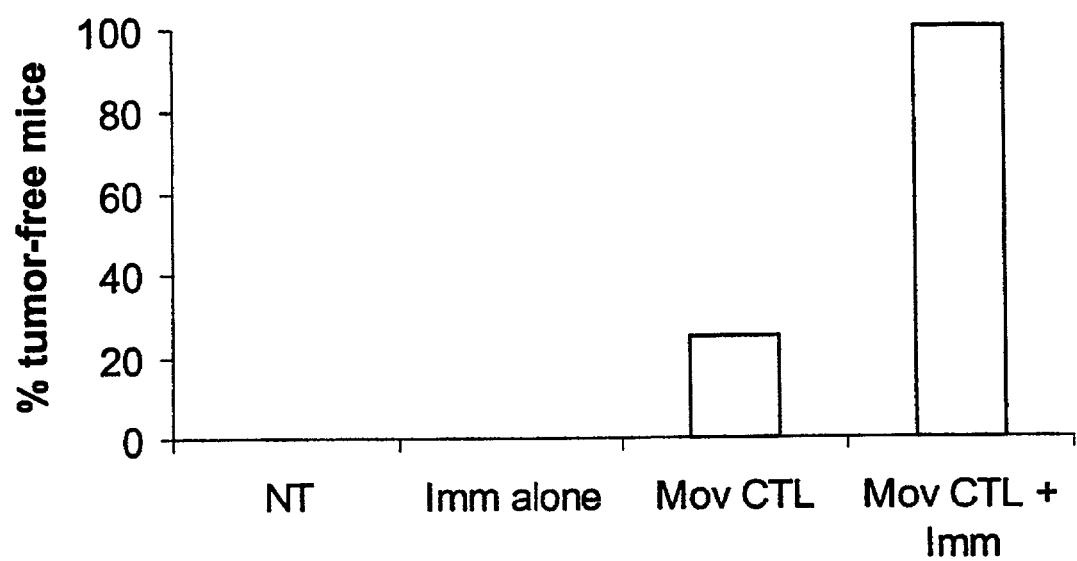
FIG. 5 shows that mice are protected against tumor challenge when infused with dual specific T cells followed by immunization with allogeneic splenocytes.

Protection Against Tumor Challenge by Adoptive Transfer of Dual Specificity T Cells C57BL/6 mice received $1 \times 10^7$ dual specificity allogeneic/MOv-γ T cells followed by subcutaneous immunization with $5 \times 10^7$ allogeneic splenocytes from donor mice 2 days later. Seven days after immunization, mice were challenged with $2 \times 10^5$ 24JK-FBP ovarian cancer tumor cells subcutaneously. The 24JK is a clone from the 3-methylcholanthrene-induced, poorly immunogenic MCA 102 murine sarcoma, where 24JK-FBP is 24JK transduced with the folate binding protein (FBP) gene, which is expressed highly on ovarian adenocarcinomas and MOv-γ is a mAb that binds FBP. Five mice per condition were then monitored for 20 days. FIG. 5 shows that in vivo immunization with allogeneic splenocytes from donor mice, in combination with administration of dual specificity T cells protected mice much more significantly than T cells alone. Specifically, the combined conditions result in 100% tumor-free mice while mice infused with dual specificity T cells alone resulted in 25% tumor-free mice.

Example 6

Figure 6:
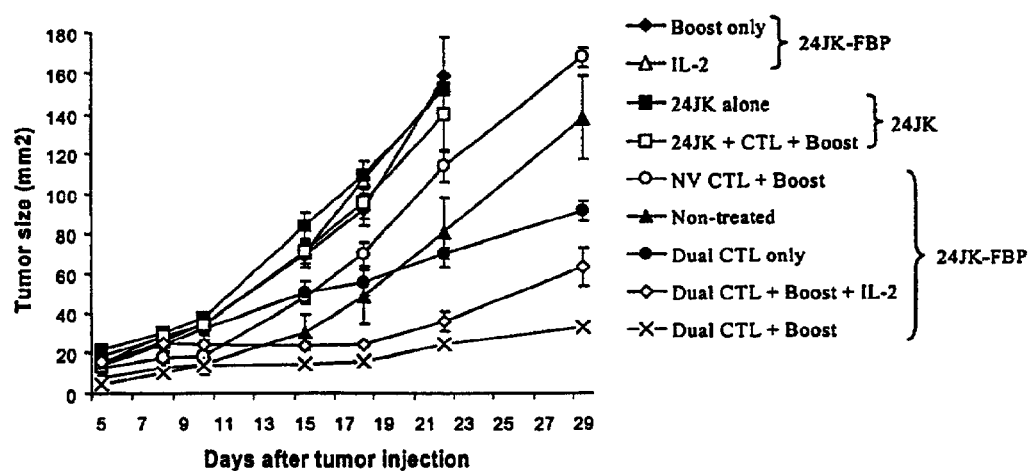
FIG. 6 shows a time course graph of the adoptive transfer of dual specific T cells followed by immunization treatment of established subcutaneous tumor in immunodeficient mice. The results show that dual specific T cells inhibit tumor growth and that the effect is augmented by immunization.

Treatment of Established Subcutaneous Tumor in Immunodeficient Mice with Adoptive Transfer of Dual Specificity T Cells Followed by Immunization In order to determine whether the combination of adoptively transferred dual specificity T cells and immunization with allogeneic cells can inhibit established subcutaneous tumors, 3 RAG-1 immunodeficient knock out mice per condition were injected on day 0 with $2 \times 10^5$ tumor cells, specifically, 24JK and 24JK-FBP tumor cells. On day 3, mice received either $1 \times 10^7$ dual specificity T cells, $1 \times 10^7$ non-transduced (NV) T cells, or no treatment. Subcutaneous immunization with $5 \times 10^7$ allogeneic splenocytes was performed on days 5, 8, and 11. On day 15, one mouse per group having a middle sized tumor was sacrificed in order to determine the effect of immunization on transferred T cell numbers. Dual specificity T cells inhibited the tumor and this effect was augmented by immunization. FIG. 6 shows that mice injected with 24JK-FBP tumor cells followed by transduced dual specificity T cells and immunization or boost, resulted in the smallest tumor size throughout the time course of 29 days.

Example 7

Generating Dual Specificity Human T Cells

Figure 7:
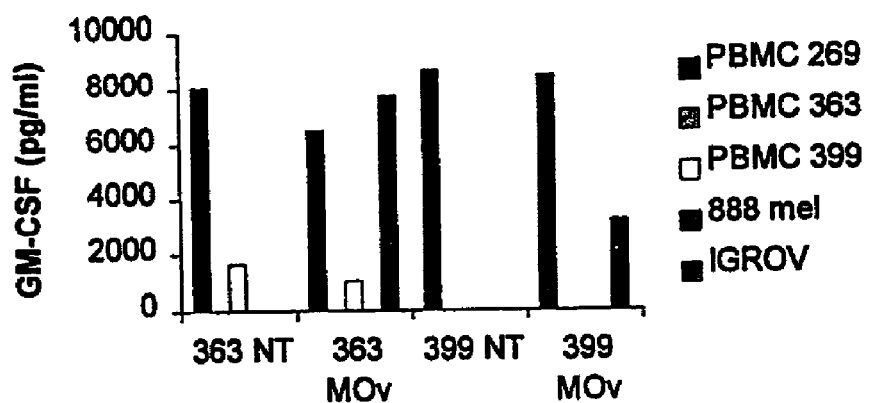
FIG. 7 demonstrates that dual specific MOv-γ transduced human T cells capable of recognizing both allogeneic cells and ovarian cancer cells can be generated in vitro by using PBMC from patients (363 and 399), transducing with MOv-γ, and stimulating with PBMC from donor (269). The graph shows that transduced and non transduced cells released GM-CSF in response to donor 269 PBMC. In addition, transduced patient (363 and 399) cells released significant amounts of GM-CSF in response to IGROV, indicating that these transduced T cells were allogeneic- and IGROV-reactive.
Figure 8A:
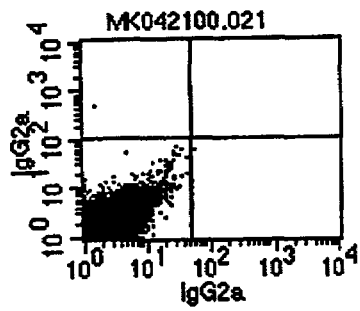
FIGS. 8A-8F shows the phenotypic results of the bulk population of T cells from patient 399 anti-269 (A-C) and of patient 363 anti-269 (D-F), where 8C and 8F demonstrate that the T cells express the chimeric MOv-γ receptor.
Figure 8D:
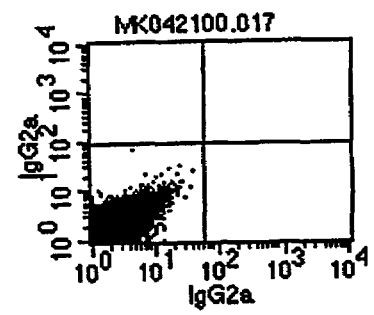
Figure 8B:
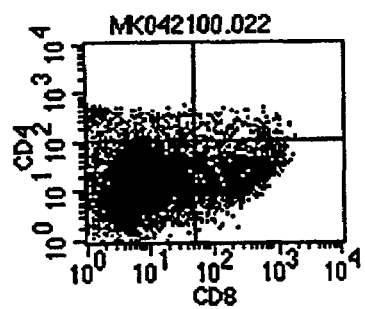
Figure 8E:
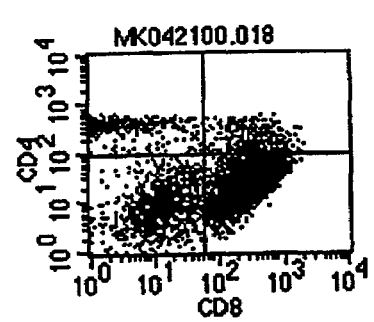
Figure 8C:
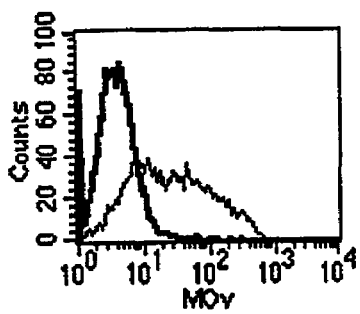
Figure 8F:
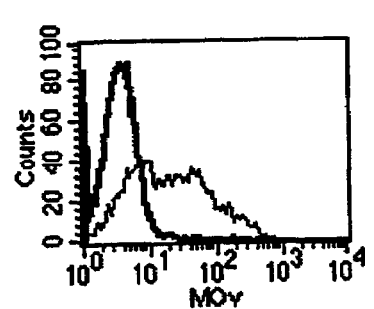

Since murine studies indicated that dual specificity T cells can be generated and functional, used for prevention, and treatment of tumors, dual specificity human T cells were generated. On day 0, $2\times10^6$ responder cells or peripheral blood mononuclear cells (PBMC) from patients 363 and 399 were cultured in the presence of $2\times10^6$ irradiated (5 Krads) stimulator cells or PBMC from donor 269 [Aim V medium (Life Technologies)/5% human serum, type AB (Valley Biomedical); 100 CU IL-2/ml] per well in a 24 well plate. On day 12 patient cells were restimulated with donor 269 PBMC ($5\times10^5$ T cells and $2\times10^6$ irradiated stimulators/well). On days 15 and 16, cultured cells were transduced with MOv-γ supernatant during centrifugation at 1000 g (2700 rpm in Sorvall tabletop centrifuge for 1 hour) in the presence of 8 μg/ml polybrene, a polycation which aids in retroviral infection. On days 18-22 cells were incubated with 0.5 mg/ml G418 (Geneticin; Life Technologies) per day for neomycin selection. On day 27 cells were restimulated with donor 269 PBMC as above. On day 35, the bulk population was assayed and cloned at 1 cell/well using standard surgery branch (SB) method with OKT3 stimulation and PBMC from another donor. Results indicated that human anti-allogeneic T cells raised from PBMC 363 and 399 against PBMC269 are both allogeneic-reactive and MOv-reactive following transduction with chimeric MOv-γ (FIG. 7). On days 49-52, the clones were characterized. The anti-allogeneic reactivity of PBMC 399 clones as measured by GM-CSF release (pg/ml) indicated that 62.5% of the clones were allo-reactive, 23.5% of the top 17 allo-reactive clones were demonstrated to be IGROV-reactive, and 12% were both allo-reactive and IGROV-reactive. The anti-allogeneic reactivity of PBMC 363 clones as measured by GM-CSF release indicated that 58% of the clones were allo-reactive, 57% of the top 7 allo-reactive clones were IGROV-reactive, and 36% were both allogeneic- and IGROV-reactive. Phenotypic characterization of the bulk population is described by FACS analysis (FIGS. 8A-8F), where FIGS. 8A-8C represent the phenotype for the bulk population of patient 399 anti-269 and FIGS. 8D-8F represent the phenotype for the bulk population of patient 363 anti-269. FIGS. 8A and 8D show the control results using non-specific IgG2a; FIGS. 8B and 8E describe the CD4 and/or CD8 phenotype of the population of cells; and FIGS. 8C and 8F show the shift of the MOv antibody-stained cells which represents the presence of the ovarian cancer (MOv)-specific receptor on T cells.

Example 8

Generating Dual Specificity T Cells and Expanding Using the SB REP Method

Figure 9:
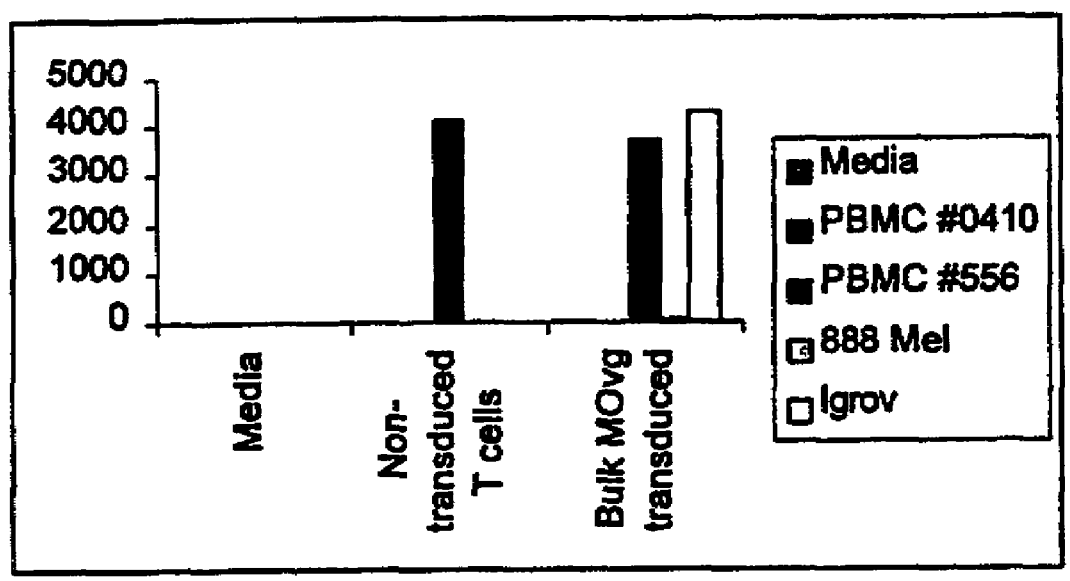
FIG. 9 shows the functional assay results from bulk MOv-γ transduced T cells of patient 410, where T cells are both allo- and IGROV-reactive as measured by GM-CSF release (pg/ml).
Figure 10A:
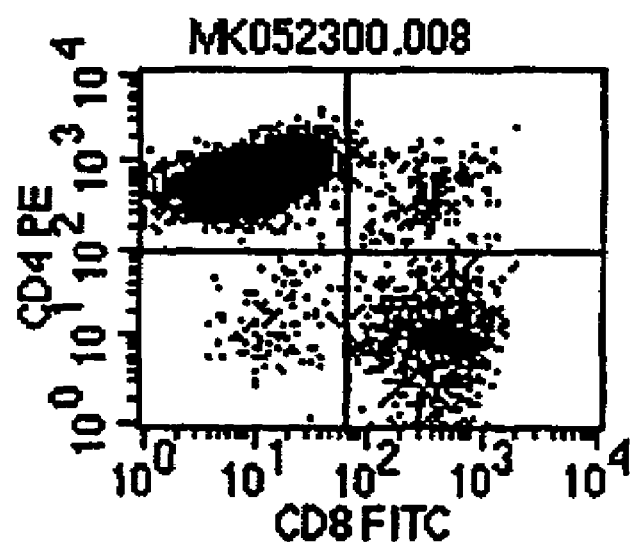
FIGS. 10A-B show the phenotypic results of bulk MOv-γ transduced T cells of patient 410 (anti-556 donor), where the T cells are primarily CD4+ and do in fact express the chimeric MOv-γ receptor.
Figure 10B:
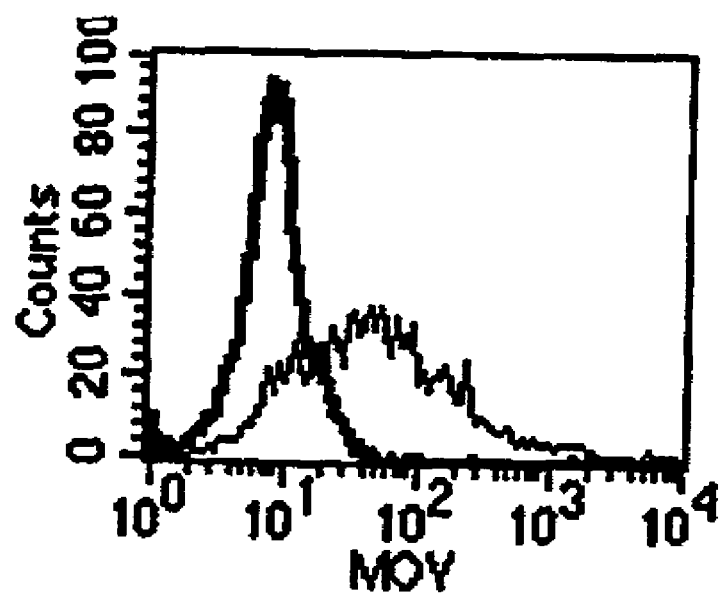
Figure 11A:
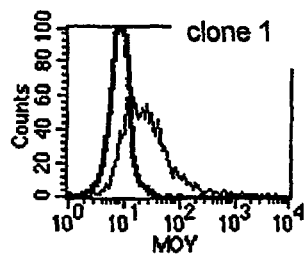
FIGS. 11A-11J show the phenotypic results of individual daughter clones from the bulk MOv-γ transduced T cells of patient 410 (anti-556 donor).
Figure 11B:
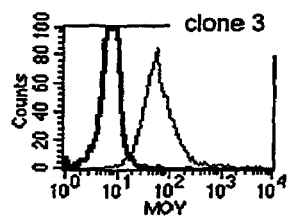
Figure 11C:
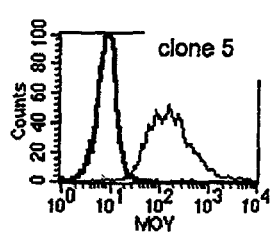
Figure 11D:
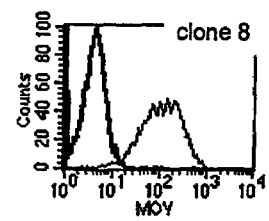
Figure 11E:
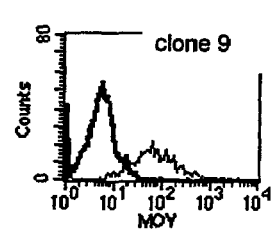
Figure 11F:
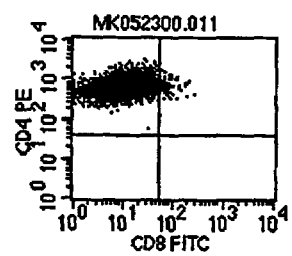
Figure 11G:
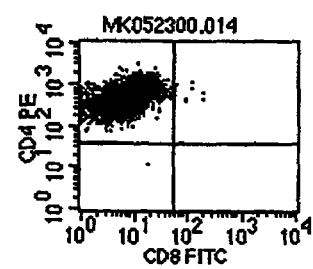
Figure 11H:
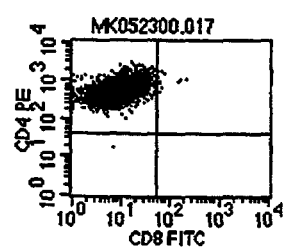
Figure 11I:
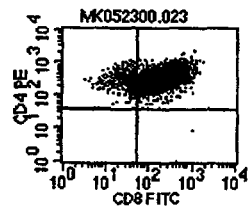
Figure 11J:
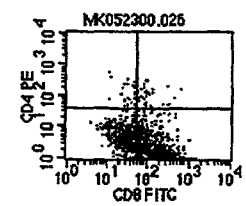

In order to determine whether or not individual T cells were both allogeneic- and MOv-γ-reactive, PBMC from patient 410 were used to generate and characterize dual specificity T cells. On day 0, $5\times10^7$ PBMC from 410 were cultured in the presence of $2\times10^6$ responders irradiated allogeneic PBMC/well from donor 556 (AIM-V/5% human serum; 100 CU IL-2/ml; in 24 well plates). On days 6 and 8, PBMC from 410 were transduced with MOv-γ supernatant supplemented with 8 μg/ml polybrene. Plates were centrifuged at 1000 g or 2700 rpm. On days 9-13, G418 selection was performed using 0.5 mg/ml per day. On day 14, the bulk population was assayed and cloned at a 1 cell/well ratio for 40 plates using standard SB method with PBMC from random donor ($5\times10^4$/well); OKT3 (30 ng/ml); and IL-2 (100 CU/ml). On days 29-31, the daughter cell clones were assayed against allogeneic and ovarian cancer targets, where 54% of 150 clones were allo-reactive and 67% of 34 clones were folate binding protein (FBP)-reactive. Therefore, 36% of the clones were shown to be reactive with both allogeneic PBMC and IGROV. On day 32, ten dual specificity clones were expanded using using random allogeneic PBMC and the SB Rapid Expansion Protocol (REP). On days 43-44, the clones were retested. The ten most reactive MOv-γ transduced T cells (410) were tested and found to be both allo- and IGROV-reactive as measured by GM-CSF release (pg/ml). The results of FIG. 9 show that non-transduced T cells are allogeneic-reactive, whereas, bulk MOV-γ transduced 410 T cells are both allogeneic- and IGROV-reactive as measured by GM-CSF release (pg/ml). FIGS. 10A-10B and Table 3 describe the phenotypic characteristic of the bulk population of patient 410 anti-556 donor cells. The majority of cells are CD4 helper T cells and were found to be reactive against IGROV. Therefore, dual specificity human T cells can be grown to recognize both allogeneic targets as well as tumor. Table 4 shows GM-CSF secretion from ten of the most reactive transduced dual specificity PBMC 410 clones. These results confirm that each clone is both alloreactive as demonstrated by the high GM-CSF release in response to PBMC 556 donor and specific for ovarian cancer as demonstrated by the high GM-CSF secretion in response to IGROV. FIGS. 11A-11J show the phenotype characterizations of representative selected clones 1, 3, 5, 8, and 9. Although there is some variation in whether the clone is CD4+, CD8+, or both CD4+/CD8+, all clones recognize the presence of the ovarian cancer specific receptor on T cells.

TABLE 3

| Quad | Events | % Gated | % Total |
|---|---|---|---|
| CD4+/CD8− | 6237 | 82.27 | 43.42 |
| CD4+/CD8+ | 233 | 3.07 | 1.62 |
| CD4−/CD8− | 116 | 1.53 | 0.81 |
| CD4−/CD8+ | 995 | 13.12 | 6.93 |

TABLE 4

| CLONE | 1 | 2 | 3 | 4 | 5 | 6 | 7 | 8 | 9 | 10 |
|---|---|---|---|---|---|---|---|---|---|---|
| PBMC410 | 1010 | 650 | 1790 | 640 | 1580 | 2380 | 2330 | 70 | 250 | 0 |
| PBMC556 | 2300 | 2410 | >5000 | 3200 | >5000 | 4870 | >5000 | 3050 | 1330 | 1020 |
| 888 mel | 105 | 0 | 20 | 0 | 750 | 130 | 100 | 0 | 0 | 10 |
| IGROV | 2820 | 2690 | 2770 | 2200 | 3440 | 4850 | 2380 | 2290 | 5270 | 2400 |

Example 9

Optimization for Generating the Highest Number of Dual Reactive T Cells

Figure 12A:
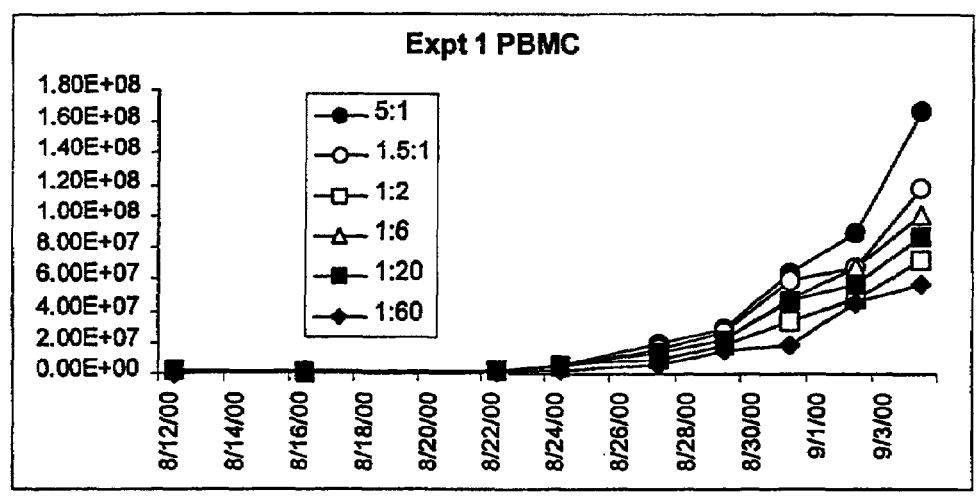
FIGS. 12A-12D show growth curve analysis of responder cells transduced with dual specific T cells following stimulation with various allogeneic cell types (PBMC, DC, or B cells) and control at varying stimulator:responder ratios.
Figure 12B:
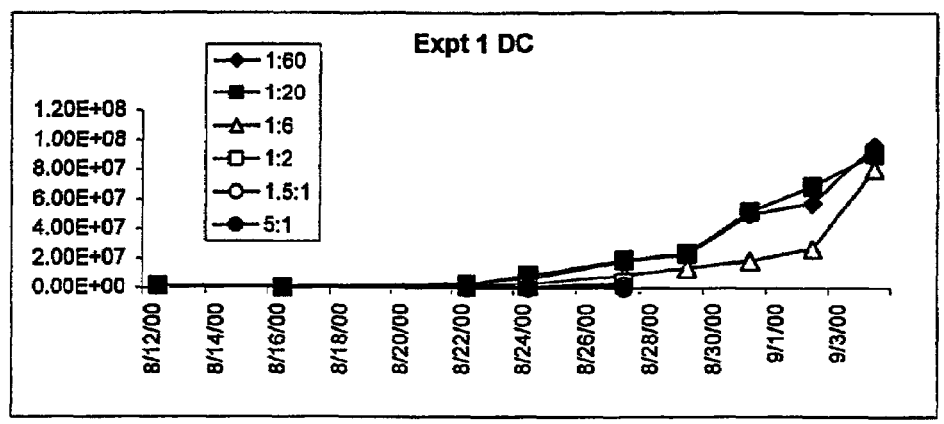
Figure 12C:
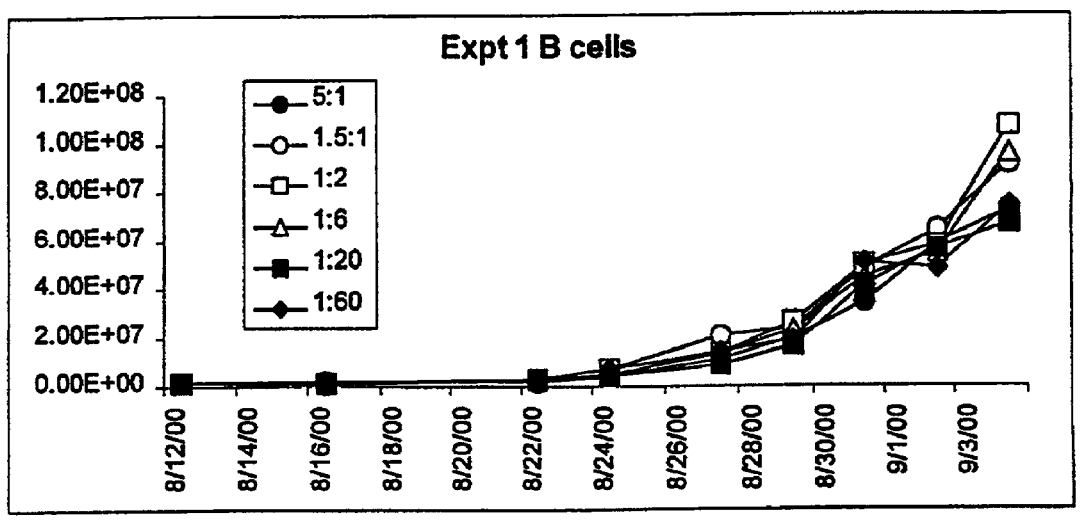
Figure 12D:
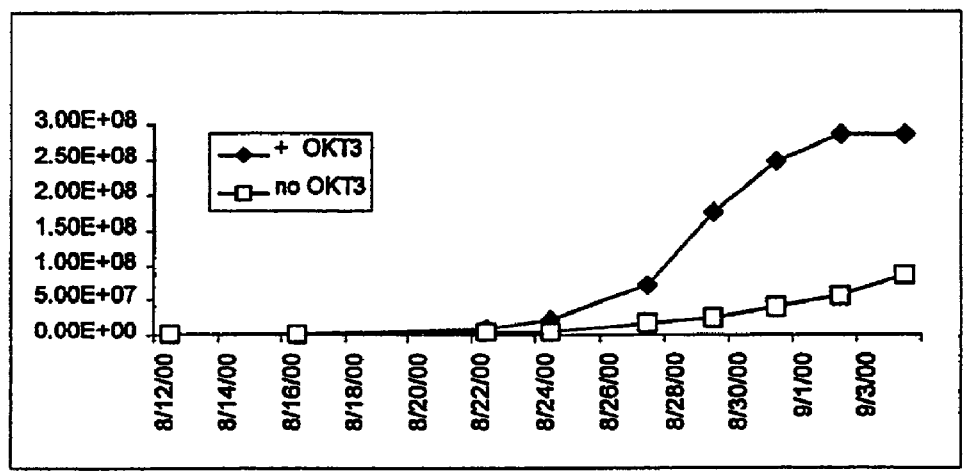
Figure 13A:
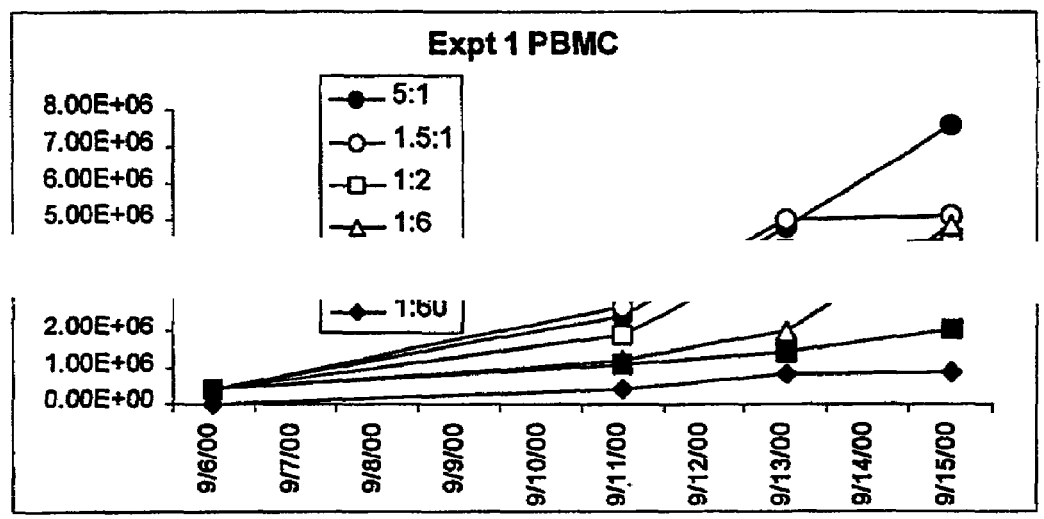
FIGS. 13A-13D show growth curve analysis of responder cells transduced with dual specific T cells following restimulation with various allogeneic cell types (PBMC, DC, or B cells) and control at varying stimulator:responder ratios.
Figure 13B:
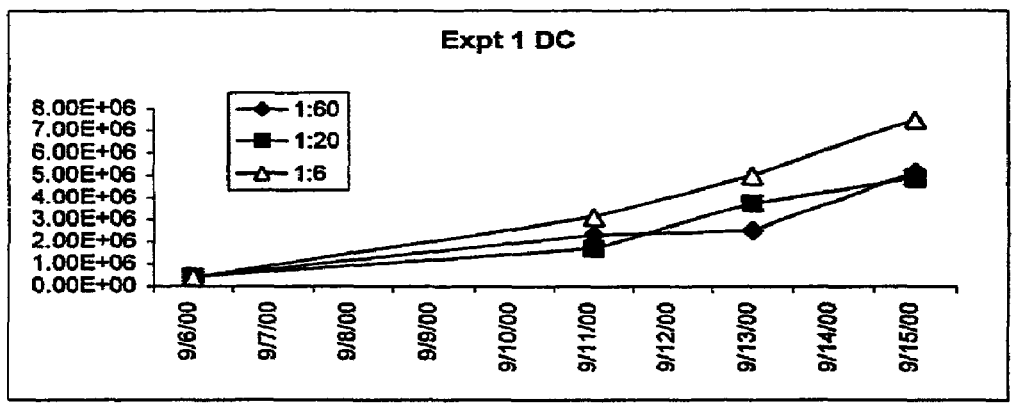
Figure 13C:
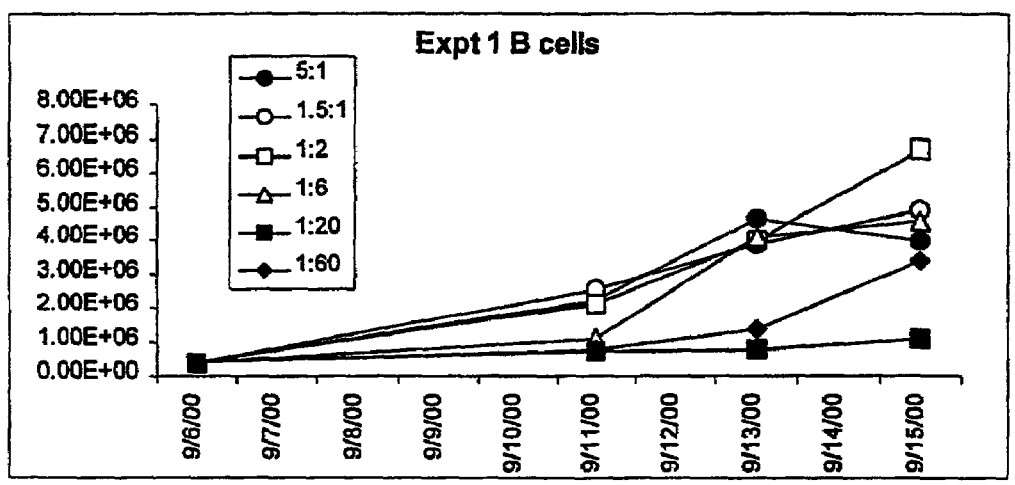
Figure 13D:
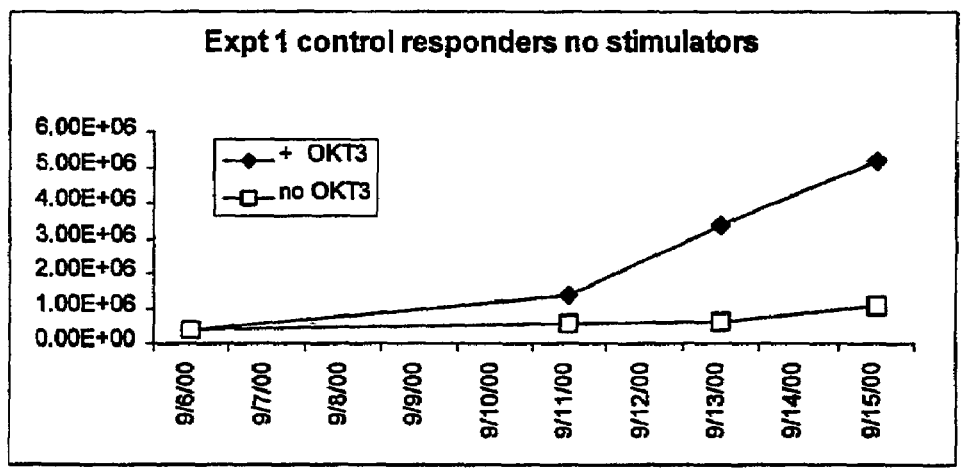

In order to maximize proliferation and reactivity against both allogeneic and tumor targets which can be utilized for patient treatment, the type of stimulator cells, the stimulator:responder ratio in MLR, IL-2 concentration, and conditions for restimulation must be optimized. Therefore, $2\times10^6$ fresh responder PBMC from a normal donor were incubated in wells of a 24 well plate with a stimulator comprising one of irradiated allogeneic PBMC, B cells, or DC at the following stimulator to responder ratios: 5:1, 1.5:1, 1:2, 1:6, 1:20, and 1:60 in AIM-V/5% human serum; 100 CU IL-2/ml). After 3 days incubation, the cells were transduced with MOv-γ/TCR by replacing ¾ of the media with retroviral supernatant followed by centrifugation at 2700 rpm for 1 hour. Transduction was repeated the following day, and cells were then selected in 0.5 mg/ml G418. FIGS. 12A-12D show growth curves following stimulation with various allogeneic cell types and at various stimulator:responder ratios. FIG. 12D is the control responder without stimulators. Table 5 describes the phenotype of T cell cultures generated from a variety of APC and stimulator to responder ratios on day 17.

Tables 6-9 show the results of functional assays of cells on day 17 after stimulation for the various APC and stimulator:responder ratios, where the different ratios were performed in duplicates. Allogeneic PBMC were determined to be good stimulators for MLR, and result in high levels of expansion when using stimulator:responder ratios ranging from 1.5:1 to 5:1. Functional assays demonstrated that transduced cells generated from PBMC stimulators were capable of recognizing allogeneic and tumor targets.

TABLE 5

| APC | Stim:Resp | CD3+ | CD4+ | CD8+ | CD4+/CD8+ | CD4+/CD8− |
|---|---|---|---|---|---|---|
| PBMC | 1:60 | 93 | 4 | 51 | 2 | 43 |
|  | 1:20 | 94 | 4 | 49 | 2 | 45 |
|  | 1:6 |  |  |  |  |  |
|  | 1:2 | 88 | 9 | 43 | 4 | 45 |
|  | 1.5:11 | 91 | 15 | 41 | 5 | 40 |
|  | 5:1 | 95 | 19 | 42 | 7 | 32 |
| DC | 1:60 | 96 | 9 | 54 | 5 | 33 |
|  | 1:20 | 99 | 25 | 44 | 10 | 21 |
|  | 1:6 | 100 | 64 | 11 | 20 | 5 |
|  | 1:2 | ND | ND | ND | ND | ND |
|  | 1.5:1 | ND | ND | ND | ND | ND |
|  | 5:1 | ND | ND | ND | ND | ND |
| B-cells | 1:60 | 90 | 10 | 41 | 4 | 45 |
|  | 1:20 | 86 | 18 | 34 | 6 | 42 |
|  | 1:6 | 88 | 25 | 28 | 8 | 40 |
|  | 1:2 | 96 | 54 | 16 | 12 | 18 |
|  | 1.5:1 | 98 | 67 | 12 | 15 | 7 |
|  | 5:1 | 99 | 76 | 10 | 11 | 3 |
| OKT3 | — | 99 | 56 | 27 | 16 | 2 |
| No OKT3 | — | 93 | 5 | 52 | 3 | 40 |

(ND = Not done)
(CD4/CD8 double negative cells were CD3+, CD19−, CD14−, CD11c−)

TABLE 6

| | PBMC (IFN gamma pg/ml) | | | | | | | | | | | |
|---|---|---|---|---|---|---|---|---|---|---|---|---|
| Stim:resp | 1:60 | | 1:20 | | 1:6 | | 1:2 | | 1.5:1 | | 5:1 | |
| media alone | 59 | 48 | 37 | 31 | 33 | 38 | 27 | 24 | 44 | 34 | 50 | 49 |
| IGROV-1 | 2785 | 2200 | 3122 | 2973 | 3320 | 2815 | 2319 | 2349 | 3251 | 3755 | 4733 | 4279 |
| 888 stim. | 185 | 614 | 165 | 172 | 65 | 66 | 38 | 42 | 65 | 69 | 100 | 91 |
| PBMC responder | 107 | 97 | 174 | 261 | 443 | 631 | 548 | 612 | 1553 | 1693 | 1802 | 1244 |
| PBMC coated OKT3 | 245 | 156 | 212 | 176 | 131 | 136 | 313 | 118 | 141 | 148 | 269 | 172 |
|  | 7018 | 7155 | 5916 | 6172 | 4950 | 6083 | 3627 | 3765 | 5078 | 5019 | >110 | 7391 |
|  |  |  |  |  |  |  |  |  |  |  |  | 60 |

TABLE 7

| Stim:resp | DC (IFN gamma pg ml) | | | | | |
|---|---|---|---|---|---|---|
| | 1:60 | | 1:20 | | 1:6 | |
| media alone | 28 | 34 | 27 | 27 | 28 | 60 |
| IGROV-1 | 2636 | 3102 | 3785 | 4131 | 1583 | 889 |
| 888 | 79 | 74 | 471 | 422 | 51 | 62 |
| stim. PBMC | 995 | 1054 | 1683 | 1463 | 1553 | 1921 |
| responder PBMC | 350 | 121 | 76 | 85 | 104 | 57 |
| coated OKT3 | 5965 | 7019 | 9385 | 9727 | 6211 | 5108 |

TABLE 8

| Stim:resp | B Cells (IFN gamma pg/ml) | | | | | | | | | | | |
|---|---|---|---|---|---|---|---|---|---|---|---|---|
| | 1:60 | | 1:20 | | 1:6 | | 1:2 | | 1.5:1 | | 5:1 | |
| media alone | 30 | 35 | 30 | 41 | 81 | 62 | 39 | 28 | 10 | 10 | 7 | 2 |
| IGROV-1 | 1374 | 1543 | 2894 | 3270 | 4634 | 3548 | 3686 | 3181 | 1583 | 1463 | 350 | 341 |
| 888 | 124 | 122 | 79 | 63 | 100 | 95 | 47 | 45 | 11 | 11 | 2 | 3 |
| stim. PBMC | 680 | 1090 | 1433 | 1314 | 1081 | 895 | 761 | 518 | 308 | 228 | 96 | 123 |
| responder PBMC | 139 | 114 | 399 | 161 | 349 | 133 | 83 | 79 | 50 | 44 | 31 | 33 |
| coated OKT3 | 7096 | 4999 | 5640 | 4871 | 6240 | 7303 | 6014 | 5916 | 5384 | 5728 | 886 | 994 |

TABLE 9

| | Stimulators (IFN gamma) | | | |
|---|---|---|---|---|
| | +OKT3 | | No OKT3 | |
| media alone | 2 | 0 | 23 | 23 |
| IGROV-1 | 1832 | 2259 | 2646 | 2587 |
| 888 | 16 | 18 | 50 | 84 |
| stim. PBMC | 16 | 17 | 43 | 72 |
| responder PBMC | 90 | 50 | 189 | 131 |
| coated OKT3 | 3656 | 3815 | 6585 | 5561 |

Following the first stimulation, $4\times10^5$ of the T cells from each group were added to the appropriate number and type of stimulator cells (from the same allogeneic donor) in a 24 well plate with 50 CU IL-2/ml and 5% AIM-V human serum. IL-2 (50 CU/ml) was added every 2 days. FIGS. 13A-13D show the number of transduced cells upon further stimulation.

Example 10

Figure 14:
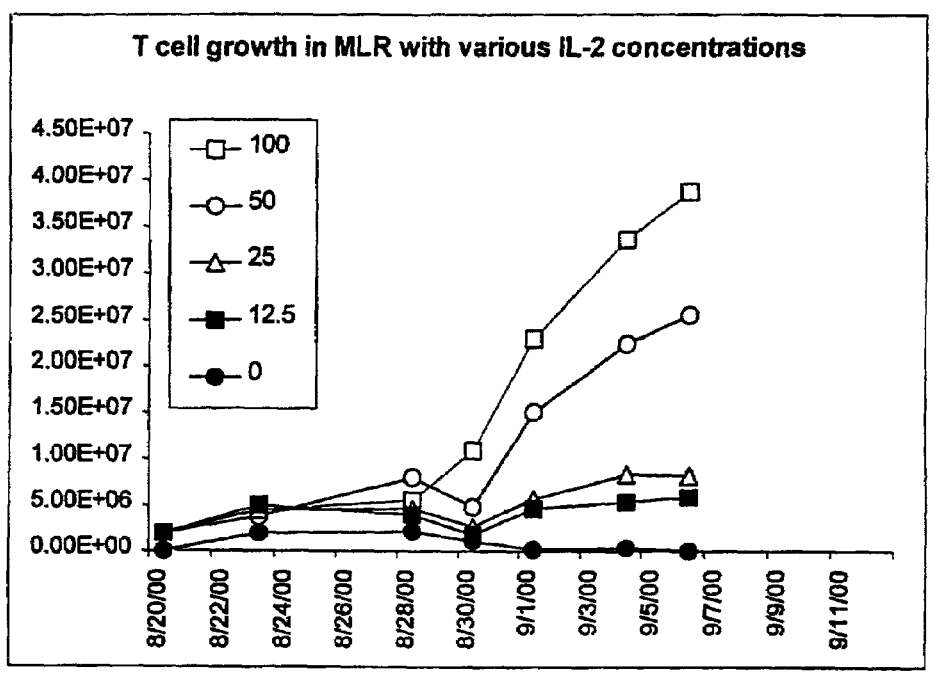
FIG. 14 shows growth curve analysis of alloreactive T cells in MLR with various concentrations of IL-2.

Optimization of IL-2 Concentrations for Maximized Cell Number and Reactivity Against Allogeneic and Tumor Targets Human alloreactive T cells from cryopreserved cells were generated using PBMC at a ratio of 1:1 ($2\times10^6$ stimulator to $2\times10^6$ responder/well), in the presence of various IL-2 concentrations. T cells were transduced with MOv-γ and selected in 0.5 mg/ml G418 for 5 days. Proliferation and reactivity against allogeneic and tumor targets were determined. FIG. 14 shows T cell growth in MLR with various IL-2 concentrations in CU/ml. Results indicate that as the concentration of IL-2 increases, the number of T cells generated also increases. The phenotypic characteristics of T cell cultures generated from a variety of IL-2 concentrations is depicted in Table 10. At all concentrations of IL-2, T cells are predominantly CD3+ and then CD4+. In Table 11, the function of MOv-γ transduced alloreactive T cells grown in a variety of IL-2 concentrations as measured by IFN-γ release (pg/ml) demonstrates that 50 CU IL-2/ml provides good expansion, as well as a high level of reactivity against both allogeneic and tumor targets.

TABLE 10

| [IL-2] | Phenotype | | | | |
|---|---|---|---|---|---|
| (CU/ml) | CD3+ | CD4+ | CD8+ | CD4+/CD8+ | CD4+/CD8− |
| 12.5 | 80 | 50 | 23 | 4 | 22 |
| 25 | 83 | 58 | 22 | 7 | 14 |
| 50 | 71 | 49 | 22 | 2 | 27 |
| 100 | 70 | 38 | 28 | 6 | 28 |

TABLE 11

| | Stimulator (IFN gamma pg/ml) | | | | | | | | | |
|---|---|---|---|---|---|---|---|---|---|---|
| | media alone | | 888 mel | | IGROV-1 | | Responder PBMC | | Stimulator PBMC | |
| media alone | 0 | 0 | 0 | 0 | 0 | 0 | 0 | 0 | 0 | 0 |
| 12.5 CU/ml IL-2 | 4 | 0 | 353 | 318 | 879 | 725 | 278 | 263 | 3900 | 3850 |
| 25 CU/ml IL-2 | 4 | 4 | 118 | 138 | 2280 | 2140 | 239 | 210 | 2420 | 3450 |
| 50 CU/ml IL-2 | 2 | 12 | 68 | 77 | 2460 | 2210 | 235 | 248 | 4880 | 4830 |
| 100 CU/ml IL-2 | 8 | 8 | 746 | 688 | 2900 | 2900 | 231 | 247 | 1850 | 2830 |

Example 11

Generation of Human Peripheral Blood Lymphocytes Transduced with the Mov-γ Chimeric Receptor Gene Serum-free AIM-V medium is supplemented with penicillin G (50 units/ml), and L-glutamine (292-584 mg/ml, 2 mM), as well as IL-2 (100 CU/ml). If necessary, AIM-V medium can also be supplemented with 1-10% human serum (type AB heat inactivated at 56° C. for 30 minutes).

PBL is isolated by leukapheresis. Lymphocytes are separated by centrifugation 1000 g (2700 rpm) on a Ficoll cushion. PBL is subjected to multiple exposures of retroviral supernatant, for up to 3 days. The PBL is then selected for 5 days in 0.5 mg/ml of the neomycin analog G418 (Geneticin; Gibco; Grand Island, N.Y.). Following G418 selection, PBL is expanded in AIM V media with 100 CU/ml IL-2. If necessary, AIM V is supplemented with 1-10% human AB serum. The exact days stated below is an approximation of what is expected for PBL transduction.

On Day 0, isolate PBMC from the leukapheresis preparation from patient and donor by Ficoll-Hypaque gradient centrifugation. Wash in $Ca^{2+}$—, $Mg^{2+}$—, Phenol red free Hanks' balanced salt solution (HBSS; BioWhittaker), then resuspend in AIM V medium supplemented with 50 CU/ml of IL-2. Irradiate donor PBMC with 5000 rads. Co-culture irradiated donor PBMC with patient PBMC at a ratio of 2:1 to 5:1.

On Day 3, harvest PBMC and resuspend in retroviral supernatant supplemented with 50 CU/ml of IL-2 and 8 μg/ml polybrene. Replate PBMC at a concentration of $1 \times 10^6$ per ml; 2 ml per well in 24 well plates. Centrifuge plates at 1000 g (2700 rpm in Sorvall tabletop centrifuge) for 1 hour.

On Day 4, remove 1 ml of media per well and replace with 1 ml of freshly thawed retroviral supernatant supplemented with 50 CU/ml of IL-2 and 8 μg/ml polybrene. Centrifuge plates at 1000 g (2700 rpm in Sorvall tabletop centrifuge) for 1 hour.

On Day 5, remove two-thirds of media per well and replace with AIM V medium supplemented with 50 CU/ml of IL-2.

On Day 6, harvest the PBL, and resuspend at $1 \times 10^6$ per ml in AIM V medium supplemented with 50 CU/ml of IL-2 and 0.5 mg/ml G418. Replate cells in appropriate size Fenwal bag (Baxter) or T-175 tissue culture flask. Aliquot $5 \times 10^6$ cells from non-transduced (NV) and transduced PBL groups for PCR analysis.

Every 2-3 days, count cells and dilute to $1 \times 10^6$ cells per ml in AIM V medium supplemented with 50 CU/ml of IL-2 and 0.5 mg/ml G418.

On day 11, harvest the PBL, and resuspend at $1.5 \times 10^6$ per ml in AIM V medium supplemented with 50 CU/ml of IL-2. Replate cells in appropriate size Fenwal bag or T-175 tissue culture flask.

Between Days 14-21, the PBL are screened for specific cytokine release against the ovarian tumor cell line IGROV-1, and phenotype by FACS analysis. Aliquot $5 \times 10^6$ transduced, selected PBL for PCR analysis. Send samples for S+L− assay for retrovirus.

On approximately day 21, the patient PBMC are restimulated with irradiated donor PBMC at a ratio of 1:1 to 2:1 (donor:patient).

The density of PBL is maintained between $1 \times 10^6$ and $2.5 \times 10^6$ PBL/ml. Once PBL have begun to grow, the cultures are assessed for growth every 3-4 days to insure that they do not increase beyond $2.5 \times 10^6$/ml.

Once the total PBL count reaches about $5 \times 10^8$, PBL are removed from the tissue culture plates or flasks and cultured further in Fenwal PL732 cell culture bags. These bags have a 1-liter capacity, but normally 500 mls medium are the maximum used in each bag. PL732 bags are gas permeable, but impermeable to fluids. Thus, oxygen and $CO_2$ are freely exchanged while tissue culture medium and cells are maintained inside. Using an inverted syringe (plunger removed), suspended by a clamp on a ring stand, connect the needle-adapter end of the syringe to the female-luer port of the 1 liter PL732 bag. Pour the cells from the 250 ml conical centrifuge tube into the bag through the syringe, and to obtain a cell concentration of $1 \times 10^6$ PBL/ml add the appropriate volume of fresh AIM-V (serum-free medium) containing the following added supplements (final concentrations): 50 units/ml penicillin G sodium (BioWhittaker), 146 g/ml L-glutamine (Media Tech), 1.25 mg/ml Fungizone, and IL-2 (50 CU/ml).

As the PBL continue to grow, they are transferred to a 3 liter capacity PL732 bag (1500 ml/bag, 1.5×109 PBL/bag) via the male- and female-luer sterile tubing ports of both the 1 liter and 3 liter bags. The appropriate volume of AIM V medium is then added to maintain the PBL at 1×106/ml. Medium is added to the 3 liter bag using the same sterile tubing attached to an inverted syringe, as described above. PL732 bags are advantageous in that access to the medium containing cells is limited to injection sites and sterile tubing ports, both of which can be maintained aseptically.

After the PBL are transferred to PL732 bags, PBL cell counts are done every 3-4 days. When the PBL density reaches $2.0 \times 10^6$/ml or greater, the PL732 bags containing medium and PBL are "split" 1:2 or 1:3 to reduce the PBL concentration to a level of $1 \times 10^6$/ml or a bit above. For example, a 1:2 split of cells at $2.0 \times 10^6$/ml involves transfer-ring 500 mls of medium (containing PBL) to a new 3 liter PL732 bag and adding 500 mls of AIM-V containing IL-2 to bring the total volume up to 1000 ml. The AIM-V being added to the 3 liter PL732 bag is transferred from a 10 liter STAK PACK of AIM-V medium (GIBCO; Life Technologies, Grand Island, N.Y.) using a sterile Solution transfer set, Life-adapter set, 81" Interconnecting jumper tube, and a Fluid fill/weigh unit.

When PBL have been expanded beyond 3 bags (about 1500 mls each), at least $4 \times 10^9$ cells (generally $1 \times 10^{10}$) may be removed for bulk freezing in a bag, keeping at least $4 \times 10^9$ PBL in culture in order to generate cells for treating the patient. For a rapidly growing culture, the PBL might be removed a week before treatment. However, for slower growing PBL might not be removed for freezing until the day of harvest. PBL are commonly used for treatment after 14-45 days in culture.

In general, PBL doubling time is 1.5 to 3 days. Thus, PBL cultures are generally split to new bags containing fresh medium every 3-5 days. Fungizone is left out of the last passage of cells in bags to minimize adverse effects on the patients. Of note, a sample is collected from the last passage of PBL for microbiology tests; this should be done 2-5 days prior to the beginning of PBL therapy. The test takes 2 days. The bags are then harvested for treatment using an automated process of cell harvesting as described by Muul, et al. *J. Immunol. Methods* 101:171, 1987).

Following the last split of cells prior to use for treatment, tests are done for bacterial and fungal contamination from samples representing 10% of the bags. If treatment occurs earlier than expected, such that Fungizone is present in the PBL growth medium, PBL harvested for treatment should be washed with 9 liters of isotonic saline, rather than the usual 3 liters. Cells can be infused with up to 75,000 CU IL-2 per infusion bag.

PBL are infused in a volume of 200-300 ml of saline supplemented with 50 ml of 25% human albumin (Alpha Therapeutic Co.). Cells are infused over 30-60 minutes through a central venous catheter. Patients receiving dual specificity cells are immunized with donor PBMC 1 and 8 days after each cell infusion. Each immunization is performed with up to $5 \times 10^9$ donor PBMC, depending on the number of cells available, administered subcutaneously in the thighs at a concentration of up to $7 \times 10^8$ PBMC per ml of injectate.

Cryopreserved, transduced PBL can be thawed for subsequent cycles or courses of therapy. If necessary, repeat transduction may be performed on either fresh PBL or cryopreserved, non-transduced PBL.

IL-2 is administered at a dose of 120,000 CU/kg as an intravenous bolus over a 15 minute period every twelve hours beginning on the day of PBL administration and continuing for up to eight doses. Doses may be skipped depending on patient tolerance. Also, if patients reach Grade III or IV toxicity (not easily reversed) due to IL-2 except for the reversible Grade III toxicities common to IL-2 such as diarrhea, nausea, vomiting, hypotension, skin changes, anorexia, mucositis, dysphagia, or constitutional symptoms and laboratory changes as detailed in Table 12, doses are not administered. If this toxicity is easily reversed by supportive measures then additional doses are given. No more than 12 doses of IL-2 is ever administered.

TABLE 12

Toxicity of Treatment with IL-2

|  | Total |
|---|---|
| Number of patients | 652 |
| Number of courses | 1039 |
| Chills | 399 |
| Pruritus | 180 |
| Necrosis | 5 |
| Anaphylaxis | 1 |
| Mucositis (requiring liquid diet) | 30 |
| Alimentation not possible | 4 |
| Nausea and vomiting | 666 |
| Diarrhea | 596 |
| Hyperbilirubinemia (maximum/mg %) | |
| 2.1-6.0 | 547 |
| 6.1-10.0 | 179 |
| 10.1+ | 83 |
| Oliguria | |
| <80 ml/8 hours | 347 |
| <240 ml/24 hours | 42 |
| Weight gain (% body weight) | |
| 0.0-5.0 | 377 |
| 5.1-10.0 | 436 |
| 10.1-15.0 | 175 |
| 15.1-20.0 | 38 |
| 20.1+ | 13 |
| Elevated creatinine (maximum/mg %) | |
| 2.1-6.0 | 637 |
| 6.1-10.0 | 85 |
| 10.1_ | 10 |
| Hematuria (gross) | 2 |
| Edema (symptomatic nerve or vessel compression) | 17 |
| Tissue ischemia | 2 |
| Resp. distress: | |
| not intubated | 67 |
| intubated | 41 |
| Bronchospasm | 9 |
| pleural effusion (requiring thoracentesis) | 17 |
| Somnolence | 114 |
| Coma | 33 |
| Disorientation | 215 |
| Hypotension (requiring pressors) | 508 |
| Angina | 22 |
| Myocardial infarction | 6 |
| Arrhythmias | 78 |
| Anemia requiring transfusion (number units transfused) | |
| 1-15 | 377 |
| 6-10 | 95 |
| 11-15 | 24 |
| 16+ | 14 |
| Thrombocytopenia (minimum/mm$^3$) | |
| <20,000 | 131 |
| 20,001-60,000 | 361 |
| 60,001-100,00 | 285 |
| Central line sepsis | 63 |
| Death | 10 |

IL-2 (Chiron), NSC #373364, is provided as a 5 mL vial containing 1.3 mg of protein as a lyophilized powder cake, with mannitol 50 mg and Sodium Dodecyl Sulfate 130 µg per milligram of protein. The 1.3 mg of protein is equivalent to approximately 21.6 million International Units (IU) or 3.6 million Cetus units (CU), where 600 IU=100 CU. The vial is reconstituted with 2.0 mL of Sterile Water for Injection, USP, and the resultant concentration is 10.8 million IU/ml or 1.8 million CU/ml. Diluent should be directed against the side of the vial to avoid excess foaming. Contents are gently swirled, not shaken, until completely dissolved. Since vials contain no preservative, reconstituted solution should be used with 8 hours.

Intact vials are stored in the refrigerator (2-8° C.) protected from light. Each vial bears an expiration date.

Reconstituted IL-2 is further diluted with 50 mL of 5% Human Serum Albumin (HSA). The HSA is added to the diluent prior to the addition of recombinant IL-2. Dilutions of the reconstituted solution over a 1000-fold range (i.e., 1 mg/mL to 1 µg/mL) are acceptable in either glass bottles or polyvinyl chloride bags. Reconstituted solutions are not mixed with saline-containing solutions. IL-2 is chemically stable for 48 hours at refrigerated and room temperatures, 2-30° C.

All patients receiving IL-2 also receive concomitant medications to relieve side effects as in all previous high-dose IL-2 protocols. The following concomitant medication begins the evening before the first dose of IL-2 and continues throughout the entire cycle of treatment: acetaminophen (650 mg every 4 hr), indomethacin (50-75 mg every 6-8 hr), and ranitidine (150 mg every 12 hr). Patients receive intravenous meperidine (25 to 50 mg) to control chills when they occur, although chills are unusual after the first one to two doses of IL-2. Ondansetron, droperidol, or scopolamine is available as needed for the treatment of nausea during treatment. Steroids are not used in these patients and if steroids are required then the patient should be taken off protocol therapy.

Example 12

"REP" Expansion of CTL clones to Therapeutic Numbers

If PBL fail to expand to adequate numbers, then cultures may be expanded using 1000 CU/ml IL-2 or the "Rapid Expansion Protocol" (REP) as described below: MOv-transduced PBL are counted and the specified number is used (Table 13). In the REP cycle immediately preceding infusion, 1.25 mg/ml Fungizone and 1 ml/L Cipro are added on day 8, and AIM V media is used.

On day 0 PBMC are thawed, washed twice in AIM V media, resuspended in complete media (CM; RPMI media) and irradiated (340 Gy) as described above. PBMC and OKT3 are added to CM, mixed well, and aliquots are transferred to tissue culture flasks. Viable cells are added last. Flasks are incubated upright at 37° C. in 5% $CO_2$. On day 2 IL-2 is added to a final concentration of 50 CU/ml.

On day 5 20 ml (130 ml for a 175 $cm^2$ flask) of culture supernatant is removed by aspiration (cells are retained on the bottom of the flask). Media is replaced with CM containing 50 CU/ml IL-2.

On day 8, an aliquot of cells is removed for counting and is further analyzed (ELISA, FACS, etc.). If cell density is greater than $1 \times 10^6$/ml, cells are split into additional flasks or transferred to Baxter 3 liter culture bags. IL-2 is added to 50 CU/ml. Fungizone is added to a final concentration of 1.25 mg/ml and 1 ml/L Cipro is added.

On day 11, IL-2 is added to a final concentration of 50CU/ml. Cells are split if density exceeds $1.5 \times 10^6$ cells/ml.

On day 14, cells are harvested and either prepared for additional REP cycles or cryopreserved. In general, REP expansion of CTL clones results in 50-200 fold expansion. Thus, 2-3 REP cycles could be required to generate a sufficient number of cells for patient treatment. If cells have grown to sufficient numbers for patient treatment, a sample is collected from each flask for microbiology tests 2-3 days before the beginning of PBL therapy (the test takes 2 days). IL-2 is added to a final concentration of 50 CU/ml on day 14 and every 3 days until the final product is prepared for infusion.

TABLE 13

| Component | 25 $cm^2$ flask | 150 $cm^2$ flask |
| --- | --- | --- |
| viable transduced PBL | $1 \times 10^5$ | $1 \times 10^6$ |
| allogeneic PBMC | $2.5 \times 10^7$ | $2 \times 10^8$ |
| OKT3 | 30 ng/ml | 30 ng/ml |
| CM | 25 ml | 75 ml |
| AIM V | | 75 ml |

Example 13

Assessment of Patient Response to Therapy

A complete response is defined as the disappearance of all clinical evidence of disease that lasts at least four weeks. Partial response is defined as a 50% or greater decrease in the sum of the products of the maximal perpendicular diameter of all measurable lesions for at least four weeks with no appearance of new lesions or increase in any lesions. A minor response is defined as a 25-49% decrease in the sum of the products of the maximal perpendicular diameters of all measurable lesions but no appearance of new lesions and no increase in any lesion.

Any patient with less than a minor response will be considered a nonresponder. The appearance of a new lesion or a greater than 25% increase in the product of perpendicular diameters of any prior lesion following a partial or complete response will be considered a relapse.

Example 14

Generation of Recombinant Viral Vector Encoding the MOv-γ Chimeric Receptor

Retroviral supernatant containing the MOv-γ chimeric receptor gene was used for lymphocyte transductions (Retroviral supernatant to be produced by Somatix, Inc, Alameda Calif.).

Figure 15:
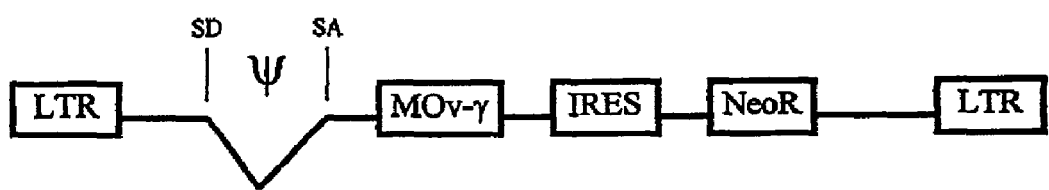
FIG. 15 shows the MFG-MOv-γ-I-N retroviral vector.

For the generation of high-titer recombinant viral vector encoding the MOv-γ chimeric receptor, the MFG-S retroviral vector and the ψ-CRIP packaging cell line were used (Danos, O. and R. C. Mulligan. Proc. Natl. Acad. Sci. U.S.A., 85:6460-6464, 1988), similar to that approved for use in ongoing clinical trials (Jaffee, et al. Cancer Res., 53:2221-2226, 1993). In the MFG-S vector, Moloney murine leukemia virus (MoMLV) long terminal repeat (LTR) sequences were used to generate both a full length viral RNA necessary for the generation of viral particles and a subgenomic mRNA analogous to the MO-MuLV envelope RNA, which is responsible for the expression of the MOv-γ gene (FIG. 15). The vector retained sequences in both the viral gag region shown to improve the encapsidation of viral RNA and the normal viral 5' and 3' splice sites necessary for generation of the subgenomic RNA. Three additional point mutations were introduced into the viral gag region to eliminate the potential expression of two overlapping open reading frames (ORFs), which encode the $NH_2$ portion of both the cell surface and cytoplasmic gag-pol polyproteins. DNA sequences encoding MOv-γ were inserted such that the initiation codon of the inserted sequences was placed precisely at the position normally occupied by the initiation codon for env translation, and minimal 3' non-translated sequences were included in the insert. The entire DNA sequence from LTR to LTR was determined for both strands of the vector and no mutations or base substitutions were discovered.

The Ψ-CRIP cell line provided the viral proteins necessary for encapsidation of recombinant retroviral genomes into infectious particles. As is the case with other packaging cell lines, the expression of the relevant viral gene products in Ψ-CRIP cells is accomplished in a manner designed to prevent the encapsidation and mobilization of the RNA molecules encoding the viral gene products. This makes possible the generation of stocks of replication-deficient recombinant virus, free of replication-competent virus.

High titer stocks of recombinant virus suitable for clinical use were generated from cultures derived from the working cell bank (WBC) propagated in a closed-loop perfusion system designed for the mass culture of anchorage dependent cells. The system allowed the culture medium to be monitored for perfusion rate, oxygen levels, and pH, permitting the growth and maintenance of large numbers of cells in a minimal volume of medium. In its current configuration, approximately $5 \times 10^{10}$ cells were cultured in a single vessel which minimized the risk of contamination from handling multiple flasks, and additionally ensured a consistent lot of recombinant virus.

To initiate a production run, a vial of the WCB of the producing cell line was thawed and expanded in culture to generate sufficient numbers of cells to seed the bioreactor. During this brief scale-up period, the cells were re-tested for sterility and mycoplasma contamination. The system was then seeded and monitored until the optimal cell density is achieved. At this point, fresh culture supernatant was collected, filtered, and stored in frozen aliquots for quality control and safety testing as required for FDA approval, followed by clinical use.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

We claim:

1. A method of preparing dual specificity T lymphocytes comprising:
   (i) contacting a population of T lymphocytes ex vivo with an allogeneic cell selected from the group consisting of dendritic cells, B lymphocytes and peripheral blood mononuclear cells (PBMCs), wherein contacting T lymphocytes with the allogeneic cell selects and specifically amplifies T lymphocytes comprising a T cell receptor that is reactive with the allogeneic cell; and
   (ii) transducing the T lymphocytes comprising the T cell receptor reactive with the allogeneic cell with a chimeric receptor gene, said gene encoding a chimeric fusion receptor between a single chain antibody that recognizes a tumor antigen and a T cell receptor capable of triggering T cell receptor signal transduction, which is reactive with a tumor antigen, to produce dual specificity T lymphocytes, wherein the dual specificity T lymphocytes generate an anti-tumor immune response in vivo.

2. The method of claim 1 said transducing comprising transducing the T lymphocytes comprising the T cell receptor reactive with the allogeneic cell with a retroviral vector comprising the chimeric receptor gene.

3. The method of claim 2, wherein the chimeric receptor comprises a single chain Fv receptor.

4. The method of claim 3, wherein the chimeric receptor is Mov-γ.

5. The method of claim 1, wherein the tumor antigen is an ovarian tumor antigen.

6. The method of claim 5, wherein the ovarian tumor antigen is folate binding protein (FBP).

7. The method of claim 1, wherein the dual specificity T lymphocytes are human T lymphocytes.

8. The method of claim 7, wherein the human T lymphocytes are lymphocytes isolated from a human.

9. The method of claim 8, wherein the human comprises an ovarian cancer, melanoma, or colon cancer.

10. The method of claim 1, said contacting comprising co-culturing the lymphocytes with allogeneic cells at a allogeneic cell:lymphocyte ratio that is about 2:1 to about 5:1.

11. The method of claim 1 further comprising contacting the lymphocytes with the cell that is allogeneic to the lymphocytes after transducing the lymphocytes with a chimeric receptor gene.

12. The method of claim 1, further comprising expanding the dual specificity lymphocytes in IL-2 containing media.

13. The method of claim 1, further comprising expanding the dual specificity lymphocytes by a Rapid Expansion Protocol (REP) comprising co-culturing the dual specificity lymphocytes with allogeneic PBMC in culture medium comprising OKT-3 and IL-2.

14. A composition comprising a population of cells comprising the lymphocytes prepared by the method of claim 1 and the cell that is allogeneic to the lymphocytes.

15. The composition of claim 14, wherein the population of cells consists essentially of the dual specificity lymphocytes and the allogeneic cell.

* * * * *

SEQUENCE LISTING

```
<160> NUMBER OF SEQ ID NOS: 4

<210> SEQ ID NO 1
<211> LENGTH: 9
<212> TYPE: PRT
<213> ORGANISM: Artificial
<220> FEATURE:
<223> OTHER INFORMATION: Synthetic

<400> SEQUENCE: 1

Thr Thr Ala Glu Glu Ala Ala Gly Ile
1               5

<210> SEQ ID NO 2
<211> LENGTH: 9
<212> TYPE: PRT
<213> ORGANISM: Artificial
<220> FEATURE:
<223> OTHER INFORMATION: Synthetic

<400> SEQUENCE: 2

Ala Ala Gly Ile Gly Ile Leu Thr Val
1               5

<210> SEQ ID NO 3
<211> LENGTH: 10
<212> TYPE: PRT
<213> ORGANISM: Artificial
<220> FEATURE:
<223> OTHER INFORMATION: Synthetic

<400> SEQUENCE: 3

Glu Ala Ala Gly Ile Gly Ile Leu Thr Val
1               5                   10

<210> SEQ ID NO 4
<211> LENGTH: 10
<212> TYPE: PRT
```

```
-continued

<213> ORGANISM: Artificial
<220> FEATURE:
<223> OTHER INFORMATION: Synthetic

<400> SEQUENCE: 4

Ala Ala Gly Ile Gly Ile Leu Thr Val Ile
1               5                   10
```